United States Patent
Earhart et al.

(10) Patent No.: US 6,300,137 B1
(45) Date of Patent: Oct. 9, 2001

(54) METHOD FOR SYNTHESIZING A SPECIFIC, SURFACE-BOUND POLYMER UNIFORMLY OVER AN ELEMENT OF A MOLECULAR ARRAY

(75) Inventors: Jonathan P. Earhart, Mountain View; Michel G. M. Perbost, Cupertino, both of CA (US)

(73) Assignee: Agilent Technologies Inc., Palo Alto, CA (US)

( * ) Notice: Subject to any disclaimer, the term of this patent is extended or adjusted under 35 U.S.C. 154(b) by 0 days.

(21) Appl. No.: 09/300,873

(22) Filed: Apr. 28, 1999

(51) Int. Cl.[7] .............................. G01N 33/00; C12Q 1/68; C12P 19/34; C07H 21/02
(52) U.S. Cl. .............................. 436/94; 435/6; 435/91.1; 536/23.1; 536/24.3; 536/24.33; 536/25.34
(58) Field of Search .............................. 436/94; 536/22.1, 536/25.3, 23.1, 24.3, 24.33; 435/6, 91.1, 91.2, 183

(56) References Cited

U.S. PATENT DOCUMENTS

| | | | |
|---|---|---|---|
| 5,445,934 | * 8/1995 | Fodor et al. | 435/6 |
| 5,464,759 | 11/1995 | Coolidge et al. | 435/91.2 |
| 5,510,476 | * 4/1996 | Ravikumar et al. | 536/25.31 |
| 5,925,525 | * 7/1999 | Fodor et al. | 435/6 |

OTHER PUBLICATIONS

Weiler et al., Combining the preparation of oligonucleotide arrays and synthesis of high–quality primers. Anal. Biochem. 243, 218–227 1996.*

Pease et al., Light–generated oligonucleotide arrays for rapid DNA sequence analysis. Proc. Natl. Acad. Sci. USA 91, 5022–5026, 1994.*

Vargeese et al., Improved coupling activators for oligonucleotide synthesis. WO 98/16540, 1–37, 1998.*

Weiler et al., Combining the preparation of oligonucleotide arrays and synthesis of high–quality primers. Anal. Biochem. 243, 218–227, 1996.*

Pease et al., Light–generated oligonucleotide arrays for rapid DNA sequence analysis. Proc. Natl. Acad. Sci. USA 91, 5022–5026, 1994.*

* cited by examiner

Primary Examiner—W. Gary Jones
Assistant Examiner—Frank Lu

(57) ABSTRACT

A method for specifically and uniformly synthesizing desired polymers within molecular array elements. Droplets containing a reactive monomer are successively applied to the elements of a molecular array in order to synthesize a substrate-bound polymer. Application of an initial droplet, having a first volume, defines the position and size of a molecular array element. Subsequent droplets are applied, to add successive reactive monomers to growing nascent polymers within the molecular array element, with covering volumes so that, even when application of the subsequent droplets is misregistered, the entire surfaces of the elements of the molecular array are exposed to the subsequently applied droplets. Following application of initial droplets, the surface of the molecular array is exposed to a solution containing a very efficient capping agent in order to chemically cap any unreacted nascent growing polymers and any unreacted substrate molecules.

19 Claims, 17 Drawing Sheets

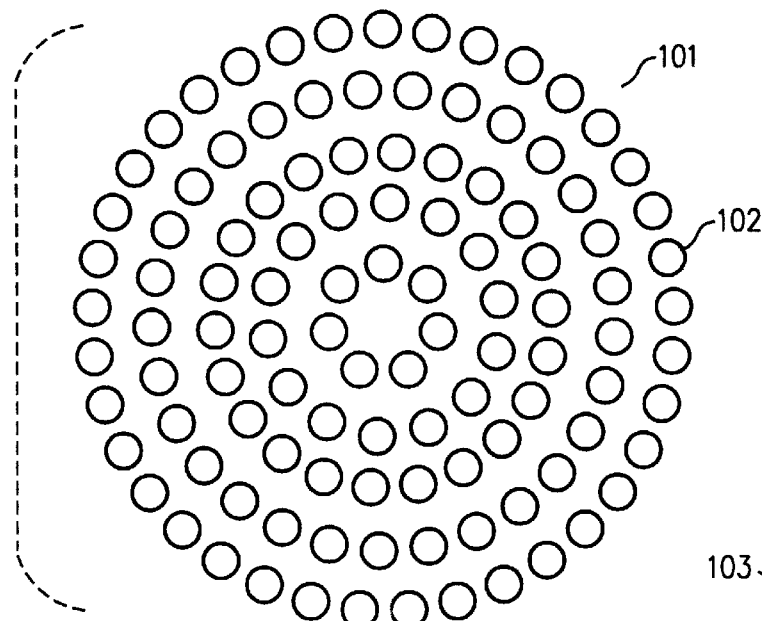
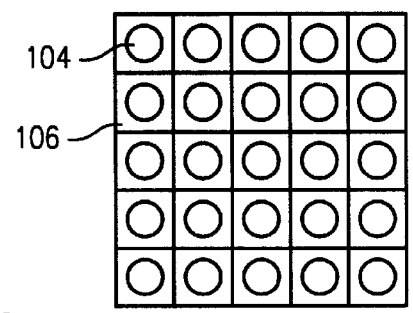
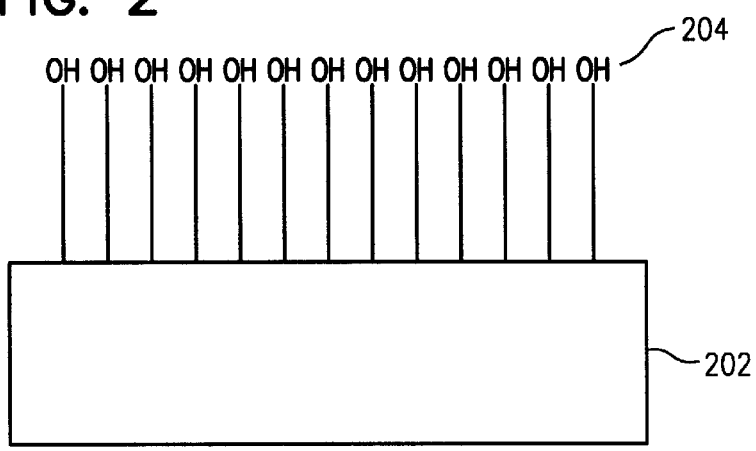

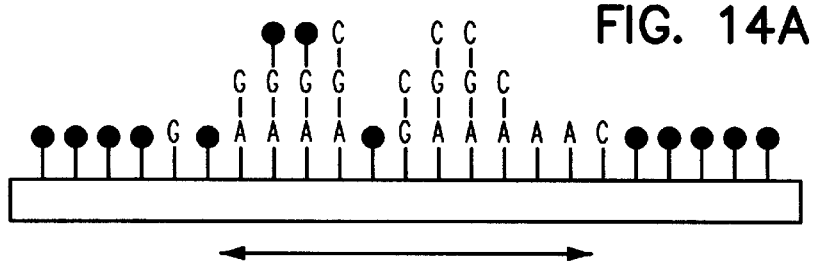
FIG. 14A
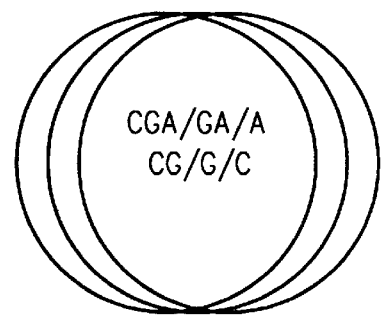
FIG. 14B
FIG. 15A
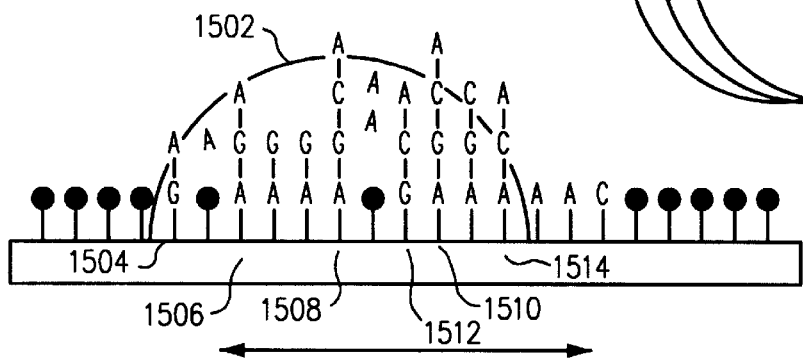
FIG. 15B
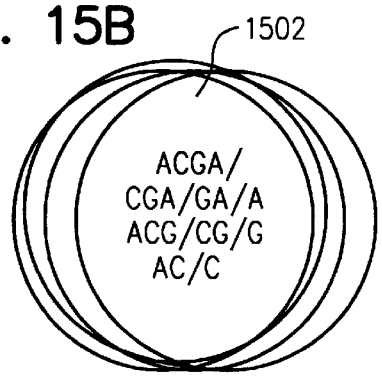
FIG. 16A
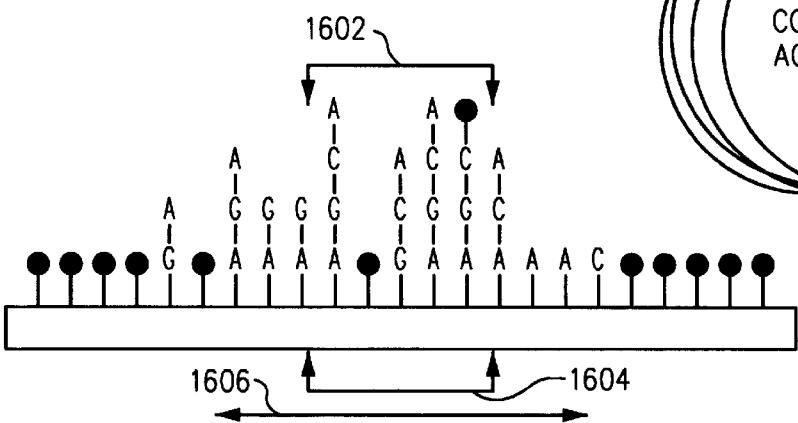

METHOD FOR SYNTHESIZING A SPECIFIC, SURFACE-BOUND POLYMER UNIFORMLY OVER AN ELEMENT OF A MOLECULAR ARRAY

TECHNICAL FIELD

The present invention relates to the synthesis of surface-bound polymers with specific predetermined sequences of monomer subunits within different elements of high-density molecular arrays and, in particular, to a method for synthesizing the surface-bound polymers with high efficiency, so that a polymer with a desired sequence of monomer subunits uniformly covers each element of the molecular array with only minimal contamination from polymers having unwanted sequences of monomer subunits within and adjacent to the element.

BACKGROUND OF THE INVENTION

A combination of synthetic chemical technologies and certain computer-related technologies has led to the development of an important analytical tool in the field of molecular biology commonly referred to as the "gene chip." Gene chips are high-density arrays of biopolymers, such as oligonucleotides or complementary deoxyribonucleic acid ("cDNA") molecules bound to a chemically prepared substrate such as silicon, glass, or plastic. In the case of oligonucleotide-containing molecular arrays, each cell, or element, within an array is prepared to contain a single oligonucleotide species, and the oligonucleotide species in a given cell may differ from the oligonucleotide species in the remaining cells of the high-density array. Gene chips may be used in DNA hybridization experiments in which radioactively, fluorescently, or chemiluminescently labeled deoxyribonucleic ("DNA") or ribonucleic acid ("RNA") molecules are applied to the surface of the gene chip and are bound, via Watson-Crick base pair interactions, to specific oligonucleotides bound to the gene chip. The gene chip can then be analyzed by radiometric or optical methods to determine to which specific cells of the gene chip the labeled DNA or RNA molecules are bound. Thus, in a single experiment, a DNA or RNA molecule can be screened for binding to tens or hundreds of thousands of different oligonucleotides.

Hybridization experiments can be used to identify particular gene transcripts in messenger RNA ("mRNA") preparations, to identify the presence of genes or regulatory sequences in cDNA preparations, or to sequence DNA and RNA molecules. Particularly in the latter application, the effectiveness of employing gene chips depends of the precision with which specific oligonucleotides can be synthesized within discrete cells of the gene chip. As with any chemical synthetic process, various factors may cause the yields of specific steps in the synthesis of oligonucleotides to be less than 100%, leading to unintended and unwanted intermediate species.

During an oligonucleotide initiation on lengthening step in the synthesis of oligonucleotides on the surface of a gene chip, reactive deoxynucleoside phosphoramidites are successively applied, in concentrations exceeding the concentrations of target hydroxyl groups of the substrate or growing oligonucleotide polymers, to specific cells of the high-density array, where they chemically bond to the target hydroxyl groups. Then, unreacted deoxynucleoside phosphoramidites from multiple cells of the high-density array are washed away, oxidation of the phosphite bonds joining the newly added deoxynucleosides to the growing oligonucleotide polymers to form phosphate bonds is carried out, and unreacted hydroxyl groups of the substrate or growing oligonucleotide polymers are chemically capped to prevent them from reacting with subsequently applied deoxynucleoside phosphoramidites. The chemical capping agents currently employed have rather low efficiencies for capping substrate hydroxyl groups, and better, but not extremely high, efficiencies for capping unreacted growing oligonucleotide polymers. As a result, each element of a molecular array may end up containing significant amounts of undesirable polymers that are unintentionally synthesized along with a desired polymer.

Molecular arrays are prepared using highly automated methods in which a series of droplets, each containing one particular type of reactive deoxynucleoside phosphoramidite, is sequentially applied to each element by a mechanical device, such as an inkjet print head. Unfortunately, the precision at which successive droplets can be applied to an element is insufficient to guarantee that each successive droplet will be confined within the boundaries of the element, or that the entire element will be covered by any particular droplet. Misregistration of successively applied droplets, like the use of inefficient capping agents, may lead to significant amounts of undesirable polymers that are unintentionally synthesized along with a desired polymer within each element, and may, in addition, lead to synthesis of unwanted polymers in regions of the surface of the molecular array substrate adjacent to each element.

The presence of undesirable polymers may lead to less specific binding of radioactively, fluorescently, or chemiluminescently labeled DNA or RNA molecules to molecular array elements, in turn leading to a significant decrease in the signal-to-noise ratio in the analysis of the molecular array and leading to spurious results. In order to automatically scan molecular arrays for the presence of radioactively, fluorescently, or chemiluminescently labeled DNA or RNA molecules, it is most desirable for the surface of the elements to be uniformly covered with desired substrate-bound polymers, and for each element to have a sharply defined edge. The inter-element surface of the molecular array substrate should have little or no contaminants that can bind DNA or RNA, including substrate-bound polymers inadvertently synthesized along with the polymers synthesized within the elements. Otherwise, after exposure of the molecular array to labeled sample molecules, fuzzy, indistinct areas of the molecular array substrate will contain labeled DNA or RNA, making it difficult for feature extraction software to select an area corresponding to an element over which to average signal intensity. Poorly averaged signal intensity may significantly lower confidence in resulting measurements, and may even produce incorrect results. Manufacturers of molecular arrays, and experimentalists and diagnosticians using molecular arrays, have therefore recognized a need for techniques for more specifically synthesizing desired polymers within molecular array elements and for uniformly covering the surface of molecular array elements with desired polymers, so that each element has a clearly defined edge and so that the inter-element regions of the molecular array substrate have as small amounts of undesirable sample-molecule-binding substances as possible.

SUMMARY OF THE INVENTION

The present invention provides a method for specifically and uniformly synthesizing desired polymers within molecular array elements. In one aspect of the present invention, a first droplet containing a specific reactive monomer is applied to the surface of a molecular array substrate at a specified position. As the droplet radially spreads out across the surface of the molecular array, the reactive monomer reacts with target molecules bound to the surface of the molecular array substrate to form a single-monomer, nascent, substrate-bound polymer within an element with boundaries defined by the area of the surface of the molecular array substrate covered by the first droplet. After first rinsing away any unreacted reactive monomer, then deactivating remaining unreacted target molecules bound to the surface of the molecular array substrate with a capping agent solution, and finally activating the single monomer of the nascent substrate-bound polymer, a second droplet having a covering volume that contains a specific reactive monomer is applied to the surface of a molecular array substrate at the specified position, resulting in addition of the specific reactive monomer in the second droplet to the activated nascent substrate-bound polymer. A covering volume is a sufficiently large volume that, even when the second droplet is somewhat misregistered with respect to the molecular array element defined by the first droplet, the entire surface of the element is exposed to the specific reactive monomer contained in the second droplet. A capping agent is then applied to the molecular array substrate to deactivate any unreacted activated nascent substrate-bound polymer. Additional droplets containing additional reactive monomers are applied in droplets having covering volumes, so that each successive droplet, after radially spreading out over the surface of the substrate, fully covers the molecular array element defined by the first droplet. Thus, despite misregistration of droplet application, the area within the molecular array element is fully exposed to the contents of all successively applied droplets, greatly diminishing synthesis of unwanted polymers within the molecular array element.

In a second aspect of the present invention, a very efficient capping agent is initially employed to prevent binding of subsequently applied reactive monomers to unreacted and uncapped target molecules bound to the surface of the molecular array substrate and unreacted and uncapped activated nascent polymers. The efficient capping agent greatly diminishes synthesis of unwanted polymers in regions of the surface of the molecular array outside of, but adjacent to the molecular array element. The combination of both aspects of the present invention provide for the automated preparation of well-defined molecular array elements uniformly covered with a desired polymer.

BRIEF DESCRIPTION OF THE DRAWINGS

FIGS. 1A–D illustrate small regions of two different types of high-density arrays containing substrate-bound oligonucleotides.

FIG. 2 illustrates, in cross-section, the surface of a high-density array prior to the synthesis of surface-bound biopolymers.

FIGS. 9A–16B illustrate the synthesis of a 4-oligonuecleotide on the surface of an HDA by a currently-available technique.

DETAILED DESCRIPTION OF THE INVENTION

Figure 3:
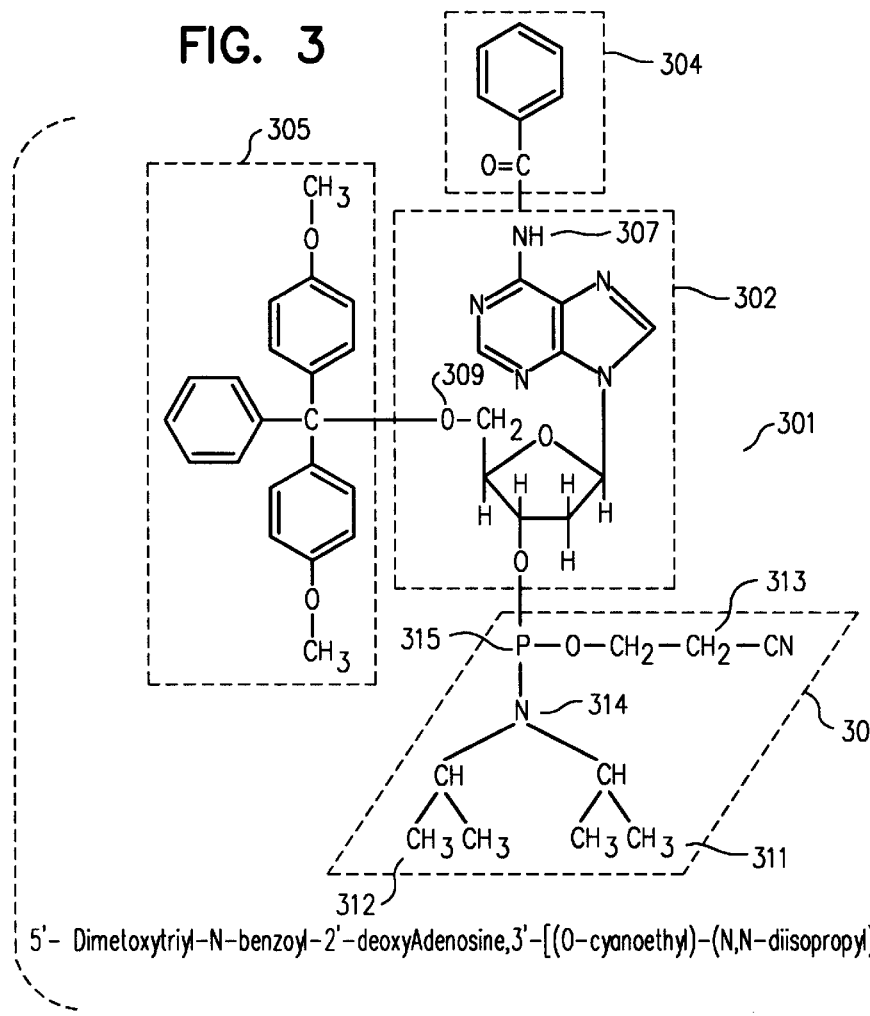
FIG. 3 illustrates the deoxynucleoside phosphoramidite 5'-Dimethoxytrityl-N-benzoyl-2'-deoxyAdenosine, 3'-[(O-cyanoethyl)-(N,N-diisopropyl)]-phosphoramidite.

One embodiment of the present invention provides a method for specifically and uniformly synthesizing desired oligonucleotides within the elements (also called cells, or features) of a molecular array. In one aspect of the present invention, a first droplet containing a specific reactive 5'-protected nucleoside phosphoramidite is applied to the surface of a molecular array substrate at a specified position. As the droplet radially spreads out across the surface of the molecular array, the 5'-protected nucleoside phosphoramidite reacts with hydroxyl groups on the surface of the molecular array substrate to form a single-nucleotide, nascent, substrate-bound oligonucleotide within an element with boundaries defined by the area of the surface of the molecular array substrate covered by the first droplet. After first rinsing away any unreacted 5'-protected nucleoside phosphoramidite, deactivating remaining unreacted surface hydroxyls with a capping agent solution, and finally activating the nascent, substrate-bound oligonucleotide by removing a dimethoxytrityl group protecting the 5-hydroxyl oxygen atom of the nascent substrate-bound oligonucleotide, a second droplet containing a specific 5'-protected nucleoside phosphoramidite having a covering volume is applied to the surface of a molecular array substrate at the specified position. As a result, the 5'-protected nucleoside phosphoramidite in the second droplet is added to the activated, nascent, substrate-bound oligonucleotide via a polymerization reaction. A covering volume is a second or subsequent droplet volume sufficient to result in the second or subsequent droplet covering the area of the surface of the molecular array substrate covered by the first droplet, even when the second or subsequent droplet is misregistered with respect to the molecular array element defined by the location at which the first droplet was applied. As a result of applying a covering volume, the entire surface of the molecular array element is exposed to the 5'-protected nucleoside phosphoramidite contained in the second droplet. A capping agent is then applied to the molecular array substrate to deactivate any unreacted deprotected nascent substrate-bound oligonucleotide. Additional droplets containing additional 5'-protected nucleoside phosphoramidites are applied in droplets having covering volumes, so that each successive droplet, after radially spreading out over the surface of the substrate, fully covers the molecular array element defined by the first droplet. Thus, despite misregistration of droplet application, the area within the molecular array element is fully exposed to the contents of all successively applied droplets, greatly diminishing synthesis of unwanted oligonucleotides within the molecular array element.

In a second aspect of one embodiment of the present invention, a very efficient capping agent is initially employed to prevent binding of subsequently applied 5'-protected nucleoside phosphoramidites to unreacted and uncapped surface hydroxyl groups and to unreacted and uncapped deprotected nascent oligonucleotides. The efficient capping agent greatly diminishes synthesis of unwanted oligonucleotides in regions of the surface of the molecular array outside of, but adjacent to, the molecular array element. The combination of both aspects of the present invention provide for the automated preparation of well-defined molecular array elements uniformly covered with a desired oligonucleotide.

FIGS. 1A–D illustrate two small regions of two different types of high-density molecular arrays ("HDAs") containing surface-bound oligonucleotides. The first type of HDA 101, shown in FIGS. 1A–B, has disk-shaped cells that each contain a particular synthesized biopolymer like, for example, cell 102. FIG. 1A shows a number of cells in a small disk-shaped region of an HDA viewed in a direction orthogonal to the surface of the HDA, and FIG. 1B shows a cross-section of the region of the HDA shown in FIG. 1A. The cells are laid out on the surface of the HDA along concentric circles, as shown in FIG. 1A, or in a matrix or gridlike arrangement (not shown). Each cell has a precisely defined location on the surface of the HDA that can be located by analytical devices that analyze labeled molecules bound to the surface of a cell using radiometric or optical methods. Biopolymers may be synthesized on the surface of the HDA in a step-wise fashion so that each cell of the HDA may contain a different biopolymer. Solutions containing the necessary reactants for the synthetic steps for creating substrate-bound biopolymers are applied in small droplets to the cells and spread in disk shaped regions of increasing radius, by surface tension and adsorption to the hydrophilic substrate, to define the cells. The inter-cell regions of the HDA surface are treated with a reagent that chemically modifies the surface of the HDA to prevent reactive monomers from covalently bonding to the inter-cell surface of the HDA during biopolymer synthesis.

FIG. 1C shows 25 cells of a square region of a second type of HDA 103 containing surface-bound oligonucleotides viewed in a direction orthogonal to the surface of the HDA. FIG. 1D shows a cross-section of the region of the HDA shown in FIG. 1C. The cells of this type HDA form a regular grid, or matrix, as shown in FIG. 1C, or are laid out along concentric circles like the HDA shown in FIG. 1A.

In one method for preparing HDAs, a device similar to the ink jet printers used for the computer-control printing of text and diagrams onto paper is used to successively deposit tiny droplets, each containing one or more specific reactants, to cells of an HDA during each synthetic step of the synthesis of substrate-bound biopolymers. Using ink jet technology, an HDA may be prepared to contain 100,000 disk-shaped cells, each having a diameter of approximately 100 microns or less, on the surface of a circular region of an HDA having a diameter of 75 mm. Each cell may be formed from a droplet with a volume on the order of 100 pl or less.

The present invention will be described in terms of a preferred embodiment related to HDAs of the type shown in FIGS. 1A–D containing oligonucleotides prepared by step-wise addition of reactive deoxynucleoside phosphoramidites to the cells. However, one skilled in the art of the preparation of HDAs will appreciate that the present invention may find application in the preparation of different types of HDAs containing other types of biopolymers prepared by step-wise polymerization of different types of reactive monomers.

FIG. 2 illustrates, in cross-section, the surface of the HDA within a cell prior to the synthesis of the biopolymers that will be bound to the surface. The substrate of the HDA 202 is prepared to present reactive functional groups, in the present case hydroxyl groups 204, at the surface that will serve as anchors to which synthesized biopolymers will be bound.

Deoxynucleoside phosphoramidites are used as reactive monomers for the step-wise synthesis of oligonucleotides. FIG. 3 illustrates the deoxynucleoside phosphoramidite 5'-Dimethoxytrityl-N-benzoyl-2'-deoxyAdenosine,3'-[(O-cyanoethyl)-(N,N-diisopropyl)]-phosphoramidite. This monomer 301 is composed of four different subcomponent groups 302–305, enclosed in FIG. 3 within dashed lines. The first subcomponent group 302 is a deoxynucleoside. In FIG. 3, the deoxynucleoside illustrated is adenosine. Other deoxynucleoside phosphoramidites used in the synthesis of oligonucleotides contain guanosine, cytidine, and thymidine in place of the adenosine 302 shown in FIG. 3. A benzoyl group 304 is linked through an amide bond to $N^6$ of the adenosine group 302. This benzoyl group protects the primary amine of the adenosine group from reacting with the phosphoramidite group of a second deoxynucleoside phosphoramidite. The primary amines of guanosine and cytidine are similarly protected in the other deoxynucleoside phosphoramidites. Different types of protecting groups are available, including, for example, acetyl or isobutyryl groups. A dimethoxytrityl ("DMTr") group 305 is linked to the 5' end of the deoxynucleoside group in order to protect the 5'-hydroxyl group of the deoxynucleoside from reacting with the phosphoramidite group of another deoxyphosphoramidite. Finally, a phosphoramidite group 303 is linked to the 3' end of the adenosine group 302. A variety of different phosphoramidite groups may be employed in which different types of alkyl groups may be substituted for the isopropyl groups 311–312 linked to the amine nitrogen atom 314 of the phosphoramidite group 303 and the cyanoethyl group 313 linked via a phosphite ester bond to the phosphorous atom 315 of the phosphoramidite group 303.

FIG. 4 illustrates the chemical steps employed to link the first protected deoxynucleoside phosphoramidite monomer to a free hydroxyl group on the surface of the HDA. A solution containing a protected deoxynucleoside phosphoramidite 402 and an activator, selected from among tetrazole, benzoimidazolium triflate ("BZT"), S-ethyl tetrazole, and dicyanoimidazole, is applied to the surface of the HDA that has been chemically prepared to present free hydroxyl groups 406. The activators tetrazole, BZT, S-ethyl tetrazole, and dicyanoimidazole are acids that protonate the amine nitrogen 404 of the phosphoramidite group of the deoxynucleoside phosphoramidite 402. A free hydroxyl group 406 on the surface of the substrate displaces the protonated secondary amine group of the phosphoramidite group by nucleophilic substitution and results in the protected deoxynucleoside covalently bound to the substrate via a phosphite triester group 408. Diisopropyl amine is released into solution. After a wash step, in which unreacted deoxynucleoside phosphoramidites, diisopropyl amine, and activator are removed, free hydroxyl groups of the substrate of the HDA, particularly free hydroxyl groups of the inter-cell regions of the substrate of the HDA 410, are acetylated 412 by application of a solution of CAP A, comprising acetic anhydride, pyridine or 2,6-lutidine (2,6-dimethylpyridine), and tetrahydrofuran ("THF"), and CAP B, comprising 1-methylimidazole in THF. After a wash step, in which the CAP A/CAP B solution is removed, the phosphite triester group is oxidized by the addition of iodine in THF, pyridine, and water to form a phosphotriester group 414.

FIG. 5 illustrates the addition of a deoxyphosphoramidite monomer to a growing oligonucleotide polymer 501 attached to the surface of the HDA. After any unreacted reagents from previous synthetic steps are removed by washing, the DMTr protecting groups of the 5'-terminal nucleosides of the growing oligonucleotides are removed by treatment with acid to produce a free 5'-hydroxyl group 502–503. Next, a protected deoxynucleoside phosphoramidite (DMTr-N-benzoyl-deoxyCytidine phosphoramidite in FIG. 5) in solution with tetrazole, or any other known activator, is applied to the substrate-bound oligonucleotide and reacts with the 5' hydroxyl of the oligonucleotide to covalently link the protected deoxynucleoside 504 to the 5' end of the oligonucleotide via a phosphite triester group 506. After excess, unreacted protected deoxynucleoside phosphoramidite and activator are removed by washing, any unreacted 5'-hydroxyl groups 508 of substrate-bound oligonucleotides are acetylated 510 by application of a CAP A (tetrahydrofuran ("THF"), pyridine, and acetic anhydride)/CAP B (methylimidazole in THF) solution. This step is necessary because the previous oligonucleotide elongation reaction does not proceed to 100% completion, and it is desirable to terminate any unreacted nucleotides by acetylation so that oligonucleotides with incorrect sequences are not produced in subsequent synthetic steps. After the CAP A/CAP B solution is removed by washing with acetonitrile, the phosphite triester group 512 is oxidized to a phosphotriester group 514 by the addition of $I_2$, THF, pyridine, and $H_2O$. The steps illustrated in FIG. 5 are repeated to add each additional deoxynucleoside to the 5' end of the growing oligonucleotide.

A particular deoxynucleoside phosphoramidite reactant can be added to each cell of the HDA during each synthetic cycle. Thus, for example, protected deoxyadenosine phosphoramidite may be added to one cell and protected deoxyguanosine phosphoramidite may be added to an adjoining cell during the first synthetic cycle. Thus, the oligonucleotide species synthesized in the first cell will have deoxyadenosine at the 3' terminus and the oligonucleotide species synthesized in the adjoining cell will have deoxyguanosine at the 3' terminus. At the completion of the synthetic cycles, each cell of the HDA may contain an oligonucleotide species having a nucleotide sequence different from the nucleotide sequences of all the other oligonucleotides synthesized in the other cells of the HDA.

Figure 6:
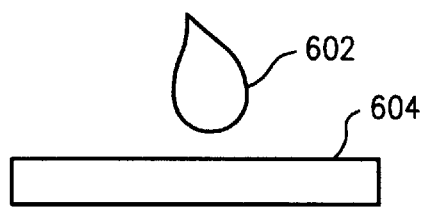
FIGS. 6–8B illustrate application of a droplet containing a protected deoxynucleoside phosphoramidite to the surface of a molecular array.
Figure 7A:
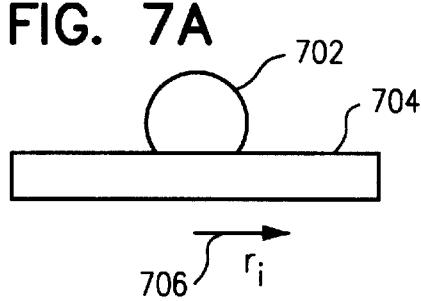
Figure 7B:
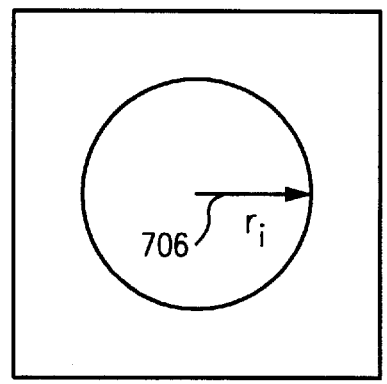
Figure 8A:
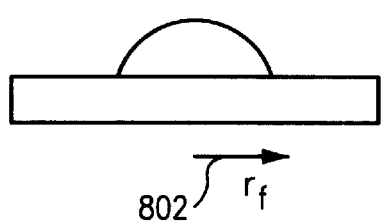
Figure 8B:
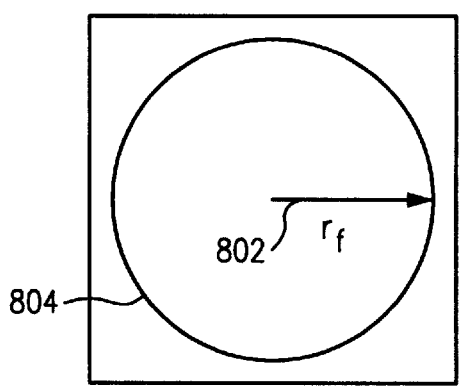

FIGS. 6A–8B illustrate application of a droplet containing a protected deoxynucleoside phosphoramidite to the surface of a molecular array. In FIG. 6, the droplet 602 is shown prior to contact with the surface of an HDA 604. FIG. 7A shows an edge-on view of the droplet 702 following contact with the surface of the HDA 704. The droplet 702 initially beads up into a semi-spherical shape with an initial radius $r_i$ 706. FIG. 7B shows a top down view of the droplet 702 immediately following application. As the solvent within the droplet interacts with the surface of the HDA, the solvent spreads out into a circular disk represented at the initial point of application of the droplet. FIGS. 8A–B illustrate an edge-on view of the solvent disk and a top-down view of the solvent disk on the surface of the HDA, respectively. The solvent disk attains a final radius, $r_f$ (802 in FIGS. 8A and 8B) that is somewhat larger than the initial radius $r_i$ (706 in FIG. 7) and that defines the radius of a cell of the HDA 804.

As discussed above, a series of protected deoxynucleoside phosphoramidite solution droplets are applied to each cell of the HDA in order to synthesize a particular oligonucleotide. The first droplet, containing the protected deoxynucleoside phosphoramidite that will end up comprising the 3'-terminal nucleoside within a synthesized oligonucleotide, defines the position of the cell on the surface of the HDA. In currently available techniques, subsequent droplets, each having a solution volume equal to the solution volume of the initial droplet, are targeted for application to the same precise location as the initial droplet. However, regardless of the method of application, subsequent droplets may end up being applied at locations offset from the location of the application of the initial droplet. The offset of a subsequent droplet from the point of application of the initial droplet is known as misregistration.

FIGS. 9–16 illustrate the synthesis of a 4-oligonucleotide on the surface of an HDA by a currently-available technique. FIG. 9A shows an edge-on view of a droplet containing protected adenosine phosphoramidite applied to a prepared surface of an HDA. In FIG. 9A, the surface of the HDA 902 has been chemically prepared to contain linker molecules with terminal OH groups, such as linker molecule 904 having terminal OH group 906. The protected adenosine phosphoramidite containing droplet 908 is shown positioned on the surface of the HDA 902. In FIG. 9A, and in subsequent figures, the droplet 908 is shown as a semi-spherically shaped droplet on the surface of the HDA. However, the semi-spherical shape is shown for clarity of display of the contents of the droplet and the interaction of the droplet with the surface of the HDA. In fact, the droplet 908 in FIG. 9A represents a somewhat flattened, disk-shaped droplet of solution with radius $r_f$ as illustrated in FIGS. 8A and 8B. The conventions employed in FIG. 9A are also employed in FIGS. 10–16, 18–23, 25–30, and 32–37, and will not be described again in subsequent discussion of those figures.

Figure 9A:
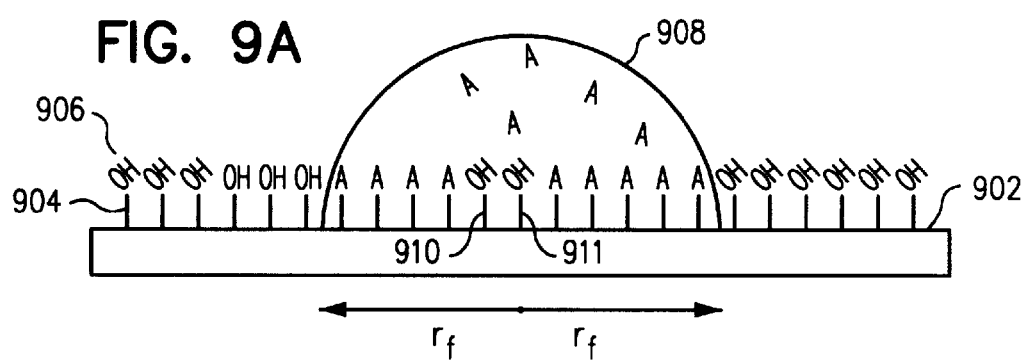
Figure 9B:
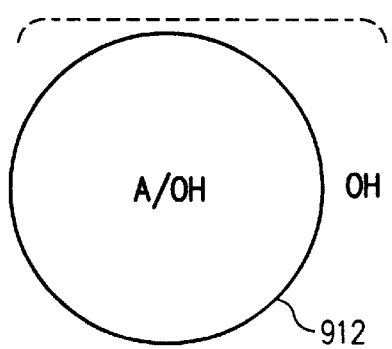

The area of the surface of the HDA in contact with the protected adenosine phosphoramidite solution 908 defines the location and shape of a cell of the HDA, as discussed above. Because the concentration of the protected adenosine phosphoramidite solution 908 greatly exceeds the concentration of terminal OH groups in contact with the solution 908 on the surface of the HDA 902, most linker molecules on the surface of the HDA in contact with the solution 908 end up bonded to protected adenosine phosphoramidite molecules, as discussed above with respect to FIG. 4A. However, as with most chemical reactions, nucleophilic substitution of the free OH groups for the protonated secondary amine group of the phosphoramidite molecule does not proceed to 100% completion. Therefore, as shown in FIG. 9A, a small fraction of free OH groups attached to linker molecules 910–911 may remain within the cell of the HDA defined by application of solution droplet 908. FIG. 9B is a top-down view of the cell of the HDA defined by application of droplet 908 in FIG. 9A. As discussed with respect to FIG. 9A, inside the cell 912 are linker molecules bound to protected adenosine phosphoramidite molecules as well as a few free OH groups of linker molecules, represented in FIG. 9B as: "A/OH." Outside the cell 912, are linker molecules bound to free OH groups.

Figure 4A:
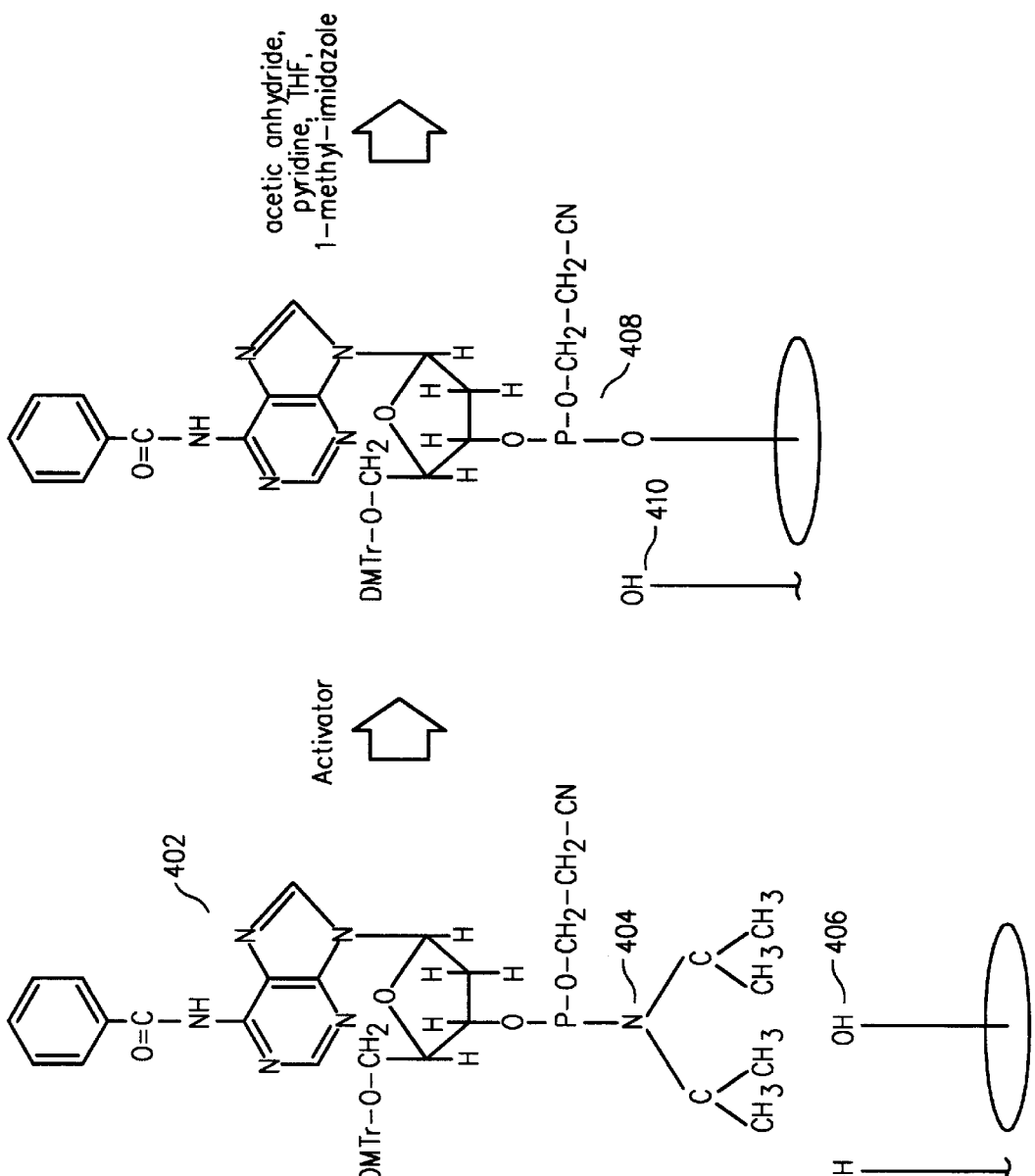
FIGS. 4A and 4B illustrates the chemical steps employed to link a first deoxynucleoside phosphoramidite monomer to a free hydroxyl group on the surface of a high-density array.
Figure 4B:
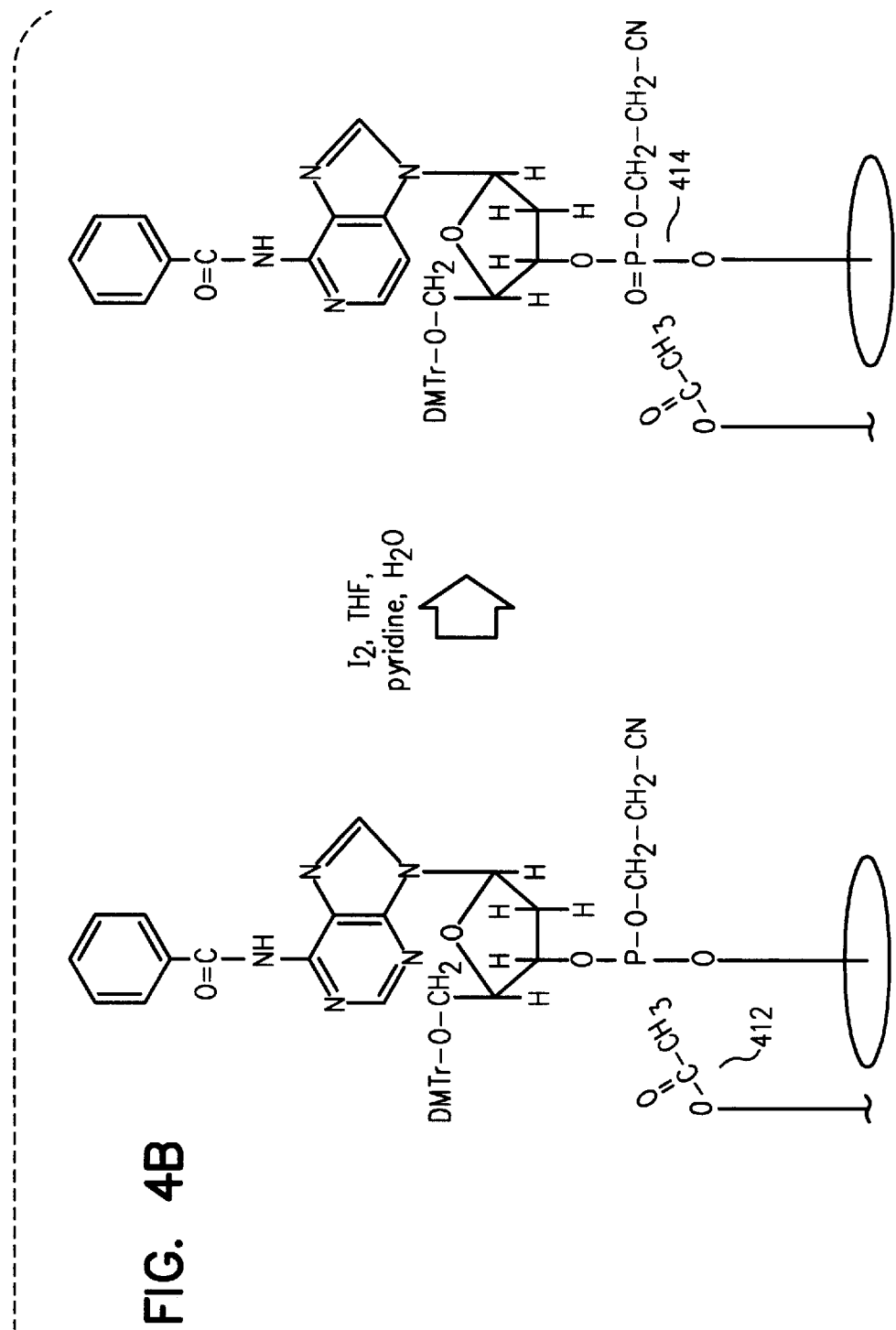
Figure 10B:
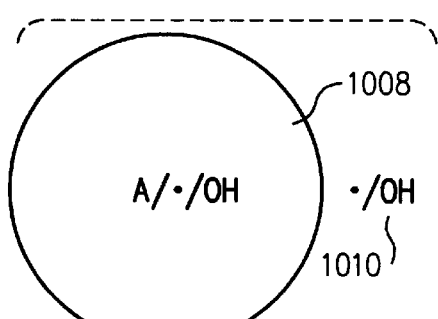
Figure 10A:
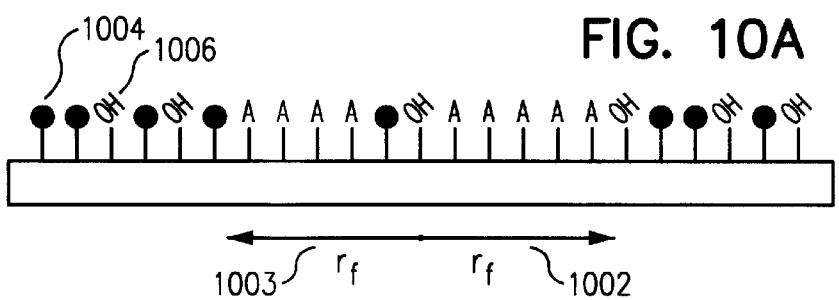

FIG. 10A shows an edge-on view of the surface of the HDA of FIG. 9A following the rinsing and acetylating steps shown in FIGS. 4A–B. The diameter of the cell, formed by application of an initial protected deoxynucleoside phosphoramidite solution, shown in FIG. 9A, is indicated by arrows 1002–1003 below the HDA substrate. Capping acetyl groups are shown in FIG. 10A as filled in disks, such as capping acetyl group 1004. The acetylating step, shown in FIGS. 4A–B, has a rather low efficiency for capping free OH groups of linker molecules of between 50–80%. Thus, a significant number of free OH groups remain uncapped, as, for example, free OH group 1006. FIG. 10B shows a representation of the cell of the HDA represented in FIG. 10A. The interior of the cell 1008 may contain protected adenosine nucleoside phosphoramidite bonded to linker molecules, acetylated linker molecules, and a very few of linker molecules with free OH groups, represented in FIG. 10B as "A/●/OH." Outside the cell 1010 are acetylated linker molecules and a few linker molecules with free OH groups, represented as "●/OH."

Oligonucleotides are commonly represented by strings of the upper case letters A, T, C, and G, that represent adenosine, thymidine, cytosine, and guanosine subunits within the oligonucleotide, respectively. The left-to-right order of the strings corresponds to a 5'-to-3' order of subunits within the oligonucleotide. This convention will be employed in the following discussion.

Figure 11A:
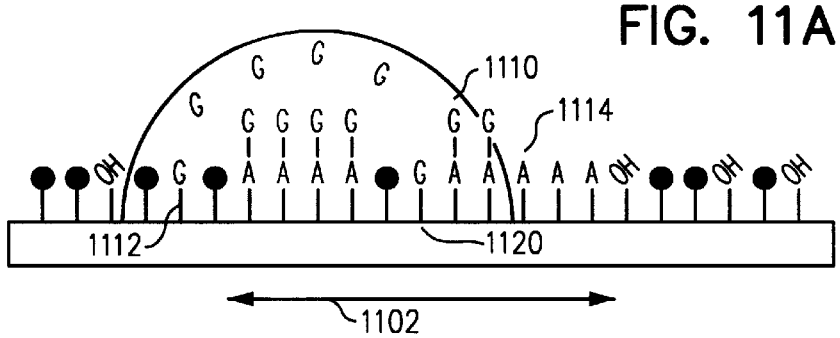
Figure 11B:
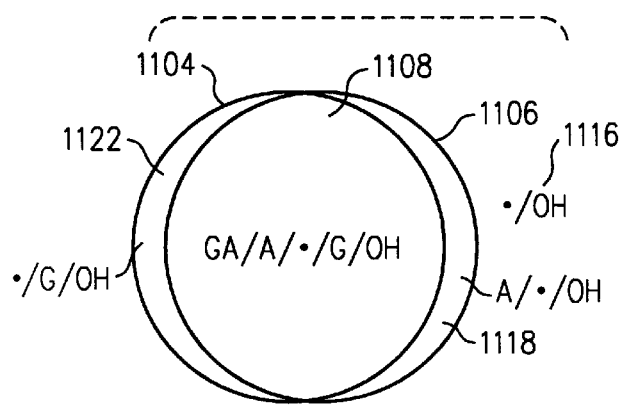

FIGS. 11A–B and 12A–12B show application of a second protected nucleoside phosphoramidite solution to the cell of the HDA defined in FIG. 9A following a deprotection step that is not illustrated. As in FIG. 10A, the diameter and location of the cell is indicated by double arms 1102 and 1202 in FIGS. 11A and 12A, respectively. Notice that, due to misregistration, the second droplet has been applied to a position to the left of the center of the cell. A top-down view of the location of the second droplet is shown in FIG. 11B. As in FIG. 11A, the second droplet 1104 is shifted, or misregistered, to the left of the center of the cell 1106. As a result of misregistration, there are now four distinct regions of the surface of the HDA in the vicinity of the cell. In the central, core region 1108, protected guanosine phosphoramidite molecules have been added to the 5'-protected adenosine molecules bound to linker molecules to form nascent GA dinucleotides, such as nascent dinucleotide 1110. Because of misregistration, certain free OH groups outside the cell have replaced the secondary amine of the protected guanosine phosphoramidite by nucleophilic substitution to produce surface-bound guanosine subunits, such as guanosine subunit 1112. Also because of misregistration, the 5'-protected surface-bound adenosine molecules at the right side of the cell, such as surface-bound adenosine group 1114, remain deprotected and unreacted with protected guanosine phosphoramidite. Thus, on adjacent regions of the surface of the HDA outside the cell and outside the area of the surface of the HDA in contact with the second droplet, there may be acetylated linker molecules and a few remaining linker molecules with free OH groups 1116. In a right-hand region of the cell 1118 outside the second droplet 1104, there may be unreacted surface-bound adenosine, acetylated linker molecules, and a few linker molecules with free OH groups. In the central core region 1108, most linker molecules are bound to nascent GA dinucleotides, but there may also be surface-bound adenosine and guanosine, such as guanosine 1120, as well as acetylated linker molecules and a very few linker molecules with free OH groups. In a small region of the surface of the HDA, in contact with the second droplet but outside the cell 1122, there may be surface-bound protected guanosine molecules as well as acetylated linker molecules and linker molecules with free OH groups. Thus, because of misregistration, instead of a single region on the surface of the HDA corresponding to the cell, there are three distinct regions 1108, 1118, and 1122 with different types of surface-bound molecules.

Figure 12A:
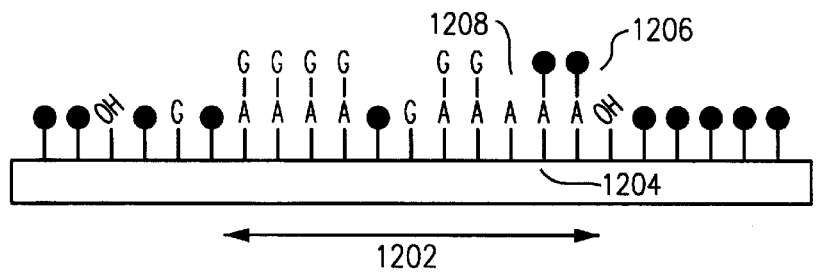
Figure 12B:
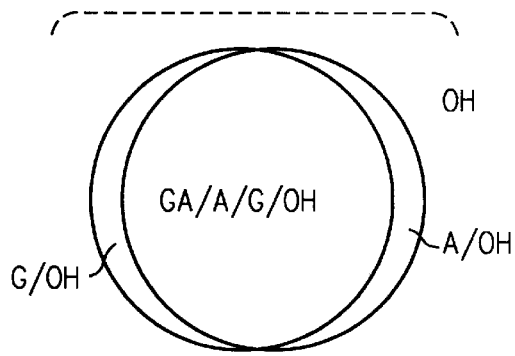

FIGS. 12A–B illustrate the cell of the HDA defined by application of the droplet in FIG. 9A following an acetylation step. The deprotected surface-bound adenosines 1204 and 1206 have been acetylated, effectively blocking further addition of nuleoside phosphoramidites to these molecules. However, as mentioned above, the acetylation step in not 100% efficient, and thus surface-bound deprotected adenosines, such as deprotected adenosine 1208, may remain within the cell. Additional linker molecules with free OH groups, not acetylated in previous steps, have been acetylated in the current acetylation step. FIG. 12B shows the contents of the various regions in the vicinity of the cell, described with reference to FIG. 11B, following the acetylation step. Note that acetylated linker molecules may be present in all regions in the vicinity of the cell, and are thus omitted in the representations of the contents of those regions in FIG. 12B and in several remaining figures, below.

Figure 13A:
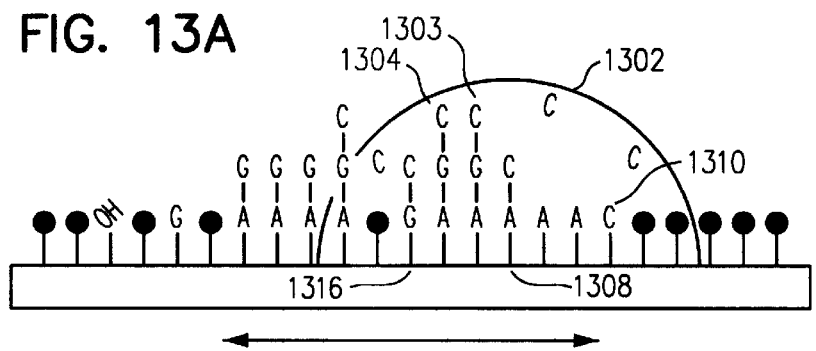
Figure 13B:
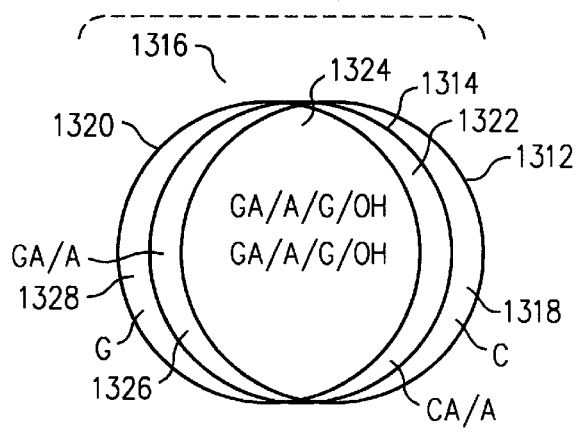

FIG. 13A shows the addition of yet another protected nucleoside phosphoramidite solution to the surface of the HDA following a deprotection step. The third droplet 1402 is misregistered, having been placed to the right of the cell. The droplet contains protected cytosine phosphoramidite, which binds via nucleophilic substitution to deprotected 5'-OH groups of surface-bound nucleotides and oligonucleotides, as well as to any remaining free linker OH groups. Thus, nascent CGA trinucleotides 1303–1304 and nascent CG 1306 and CA 1308 dinucleotides may now be bound to the surface of the HDA. In addition, a few cytosine molecules may be bound directly to linker molecules 1310. FIG. 13B shows a top-down view of the third protected nucleoside phosphoramidite solution droplet on the surface of the HDA. Misregistration of the third droplet 1312 with respect to the cell 1314 produces six distinct regions on the surface of the HDA in the vicinity of the cell. Outside the cell and the areas of application of the second and third droplets 1316, the surface of the HDA is covered primarily with acetylated linker molecules, with a few remaining linker molecules having free OH groups. In a right-hand region of the third droplet 1318, that does not overlap with the cell 1314 or the second droplet 1320, the surface may contain cytosine nucleotides attached to linker molecules. In a right-hand region of the cell 1322, the surface of the HDA may contain nascent CA oligonucleotides as well as acetylated adenosine nucleotides attached to linker molecules. A central core region 1324 contains primarily CGA nascent oligonucleotides, as well as small amounts of acetylated GA oligonucleotides and protected CG oligonucleotides, and adenosine, guanosine, and cytosine nucleosides bound to linker molecules. In a left-hand section of the cell 1326, the surface of the HDA may contain deprotected GA oligonucleotides and adenosine nucleosides directly attached to linker molecules. Finally, in a left-hand portion of the region covered by the second droplet 1328 not overlapping the cell 1314 or the third droplet 1312, the surface of the HDA may contain guanosine nucleosides directly attached to linker molecules. Note that in FIG. 13B, the presence of free OH groups is no longer represented. In general, after a number of acetylation steps, it is expected that the linker molecules will be nearly completely acetylated. FIGS. 14A and 14B show edge-on and top-down views of the surface of the HDA in the vicinity of the cell following an additional acetylation step.

FIGS. 15A–B show application of a fourth protected nucleoside phosphoramidite solution droplet to the surface of the HDA. The fourth droplet 1502 is again misregistered, positioned somewhat to the left of the cell. The fourth droplet contains protected adenosine phosphoramidite which binds via the nucleophilic substitution to the protected 5'-terminal residues of nascent oligonucleotides. Because of misregistration, the protected adenosine phosphoramidite may bind to surface-bound guanosines 1504 and GA oligonucleotides 1506 as well as to CGA trinucleotides 1508 and 1510 and CG 1512 and CA 1514 dinucleotides. FIG. 15B shows a top-down view of the surface of the HDA in the vicinity of the cell following addition of the fourth protected nucleoside phosphoramidite solution droplet. Again, because of misregistration, a number of surface regions have been created, in addition to the core region 1502. The contents of these regions are becoming somewhat complicated, and will not be discussed in detail. The core region primarily contains nascent ACGA oligonucleotides, along with much small concentrations of CGA surface-bound trinucleotides, nascent surface-bound ACG trinucleotides, nascent surface-bound AC dinucleotides, GA and CG dinucleotides, and adenosine, guanosine, and cytosine nucleosides.

Figure 16B:
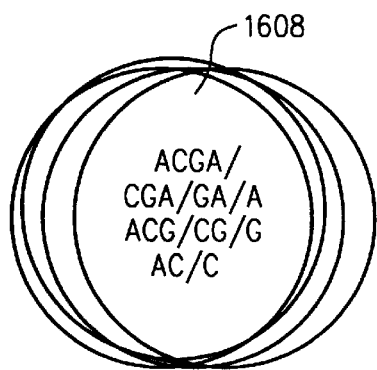

FIGS. 16A–B show an edge on view and a top-down view of the cell of the HDA following an additional acetylation step. In FIG. 16A, the central core region of the cell that contains primarily ACGA surface-bound oligomers is indicated by double arrows 1602 and 1604. Note that this central core region is approximately centered within the cell whose diameter and position is indicated by double arrows 1606. The central core region and possible surface-bound constituents of the central core region 1608 is shown as an irregularly shaped region in FIG. 16B.

Figure 17:
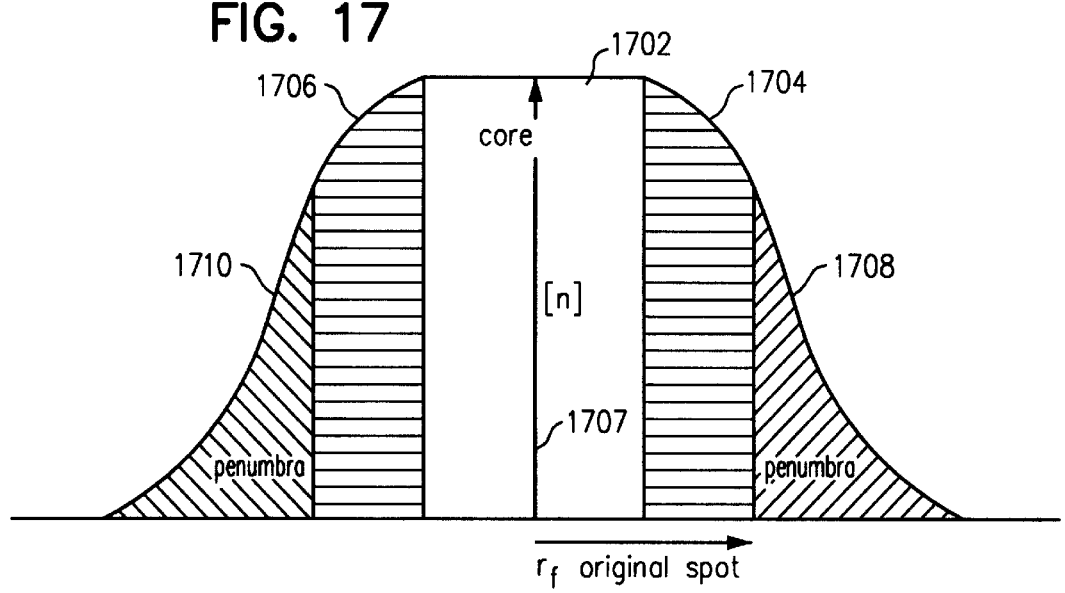
FIG. 17 is a graphical representation of the contents of the surface of he HDA in the vicinity of the cell, as represented in FIG. 16A–B.

FIG. 17 is a graphical representation of the contents of the surface of the HDA in the vicinity of the cell, as represented in FIGS. 16A–B. Centered within the cell is a core region 1702 (indicated by double arrow 1602 and 1604 in FIGS. 16A). This central core region primarily contains surface-bound ACGA oligonucleotides. The possible surface-bound nucleotides and oligonucleotides within the core is shown below:

```
A C G A
      A
    G A
  C G A
    G
  C G
A C G
  C
A C
```

While the main surface-bound constituent of the core is the four-nucleoside oligonucleotide ACGA, shorter oligonucleotides may also be present. The shorter oligonucleotides present in the core region 1702 may include all possible subsequences of the sequence ACGA, as shown above.

Surrounding the central core region 1702 within the cell are two peripheral regions 1704 and 1706 corresponding to the surface of the cell not included within the core region 1702. In this peripheral region of the cell, the total concentration of oligonucleotide subunits, represented by the vertical axis 1707, is somewhat less than in the core region, since, because of misregistration, not all solution droplets in the sequence of solution droplets applied to the cell are applied to the peripheral region. The peripheral region may contain all of the oligonucleotides contained in the core region, as shown above, but may, in addition, contain the oligonucleotides: CA, AG, AGA, ACA, and AA. These additional oligonucleotides do not represent subsequences of the sequence ACGA, but instead represent subsequences from which one or more subunits have been deleted. These deletion subsequences are problematic. They may be complementary to, and bind, sample DNA that does not contain sequences complementary to the sequence ACGA.

Thus, the cell of the HDA, because of misregistration and incomplete acetylation, is contaminated with spurious oligonucleotides that may bind labeled sample molecules that should not, in the ideal case of complete acetylation and accurate droplet application, be bound to the cell. This may result in a low signal-to-noise ratio or to false results. Finally, there is a penumbral region 1708 and 1710 exterior to the cell, but adjacent to the cell, that may contain any of the partial sequences contained in the core region 1702 or deletion sequences contained in the peripheral region 1704 and 1706. Again, sample molecules may end up being bound to these contaminating oligonucleotides in the penumbral region to produce low signal-to-noise ratios or false results.

In the example of FIGS. 9A–16B, a 4-nucleoside oligonucleotide is synthesized. However, significantly longer oligonucleotides are generally prepared on HDAs used for research and diagnosis. The problems illustrated in FIGS. 7A–16B are compounded with each additional synthetic step. Moreover, each different subsequence contaminating the core region may significantly lower the desired specificity of binding of an HDA cell.

Figure 18:
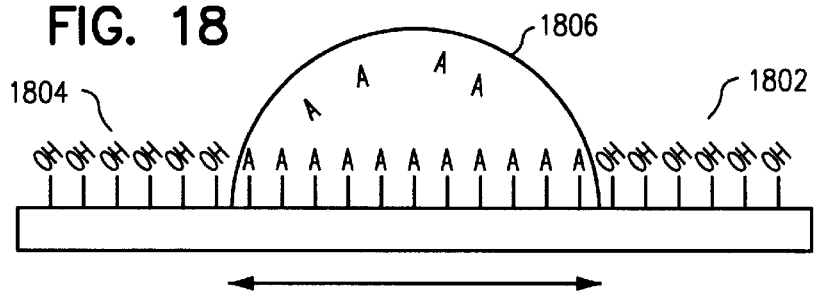
FIGS. 18–24 illustrate a first improved technique for applying protected nucleoside phosphoramidite solution droplets to the surface of the HDA during synthesis of oligonucleotides on the surface of the HDA.
Figure 19:
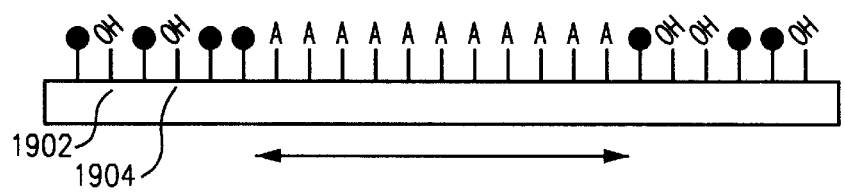

FIGS. 18–24 illustrate a first improved technique for applying protected nucleoside phosphoramidite solution droplets to the surface of the HDA during synthesis of oligonucleotides on the surface of the HDA. FIGS. 18–24 illustrate synthesis of the same four-nucleoside oligonucleotide ACGA as synthesized in the example illustrated in FIGS. 9–16. FIG. 18 shows a first protected adenosine phosphoramidite solution droplet applied to the HDA to define a cell. In this example, the complex, fractional oligonucleotide subsequences arising from incomplete acetylation within the cell are not shown, to simplify illustration of the example. In FIG. 18, the surface of the HDA external to the droplet contains linker molecules with free OH groups 1802 and 1804, while the surface of the HDA within the cell defined by the solution droplet 1806 contains surface-bound adenosine resulting from nucleophilic substitution of linker OH groups for the secondary amine of the protected adenosine phosphoramidite. FIG. 19 shows the surface of the HDA following an acetylation step. Note that, as in FIG. 10A, acetylation of linker OH groups is incomplete.

Figure 20:
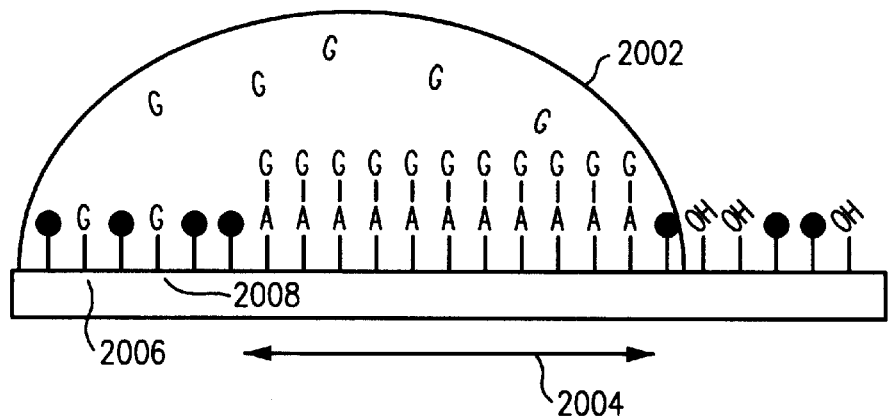

FIG. 20 shows application of a second protected nucleoside phosphoramidite solution droplet to the surface of the HDA. As in FIG. 11A, application of the second droplet 2002 is misregistered, or offset from the center of the cell. However, according to the first improved technique, the volume of the second droplet is substantially greater than the volume of the first droplet (1806 in FIG. 18) that defined the location and shape of the cell. Because the volume of the second droplet 2002 is greater than that of the first droplet (1806 in FIG. 18), the entire surface of the cell, indicated by double arrow 2004, is in contact with the second droplet containing protected guanosine phosphoramidite. Therefore, all of the deprotected substrate-bound adenosine binds, by nucleophilic substitution, to the protected guanosine phosphoramidite with release of the protonated secondary amine. Thus, following application of the second droplet 2002, the cell contains primarily nascent dinucleotide GA. However, as in FIG. 11A, the free OH groups (1902 and 1904 in FIG. 19) have also bound, via nucleophilic substitution, to protected guanosine phosphoramidite in the second droplet 2002 resulting in substrate-bound protected guanosine 2006 and 2008.

Figure 21:
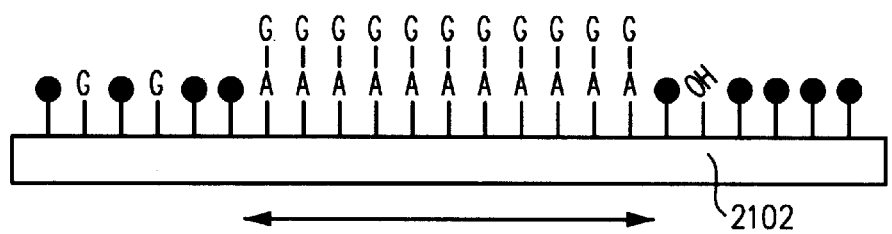
Figure 22:
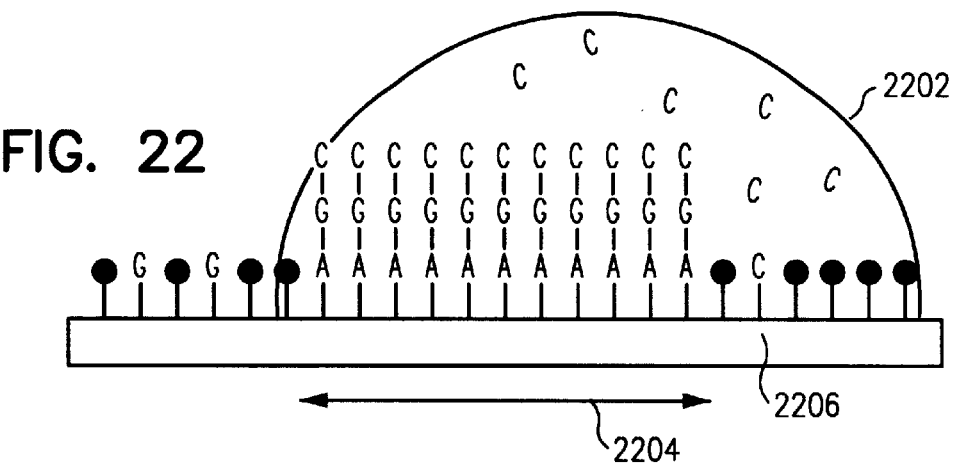
Figure 23:
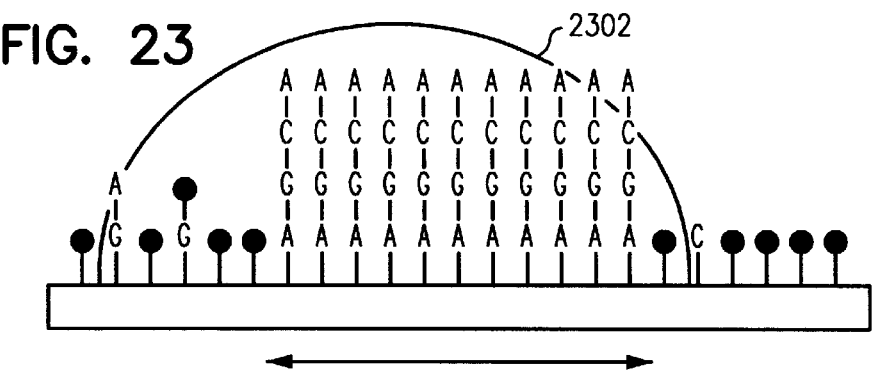

FIG. 21 shows an edge-on view of the cell following an acetylation step. FIG. 22 shows application of a third protected nucleoside phosphoramidite solution droplet to the cell of the HDA. Again, in FIG. 22, a larger volume protected nucleoside phosphoramidite solution droplet 2202 has been applied to the surface of the HDA, misregistered to the right as in FIG. 13A. However, again because of the larger volume of the droplet 2202, the entire surface of the cell, indicated by double arrow 2204 is in contact with the third droplet 2202. Thus, the surface of the cell contains primarily the nascent trinucleotide CGA. However, as in FIG. 13A, free OH groups outside the cell (2102 in FIG. 21) may end up binding to the protected cytosine phosphoramidite to form substrate-bound cytosine 2206. FIG. 23 shows addition of a fourth droplet containing protected adenosine phosphoramidite. Again, the fourth droplet 2302 is misregistered to the left of the cell, as in FIG. 15A. However, because of the larger volume of the fourth droplet 2302 than the initial droplet that defined the size and location of the cell (1806 in FIG. 18), the entire surface of the cell is exposed to the fourth droplet 2302. Therefore, the protected adenosine phosphoramidite in the fourth droplet 2302 reacts with the protected 5' cytosine of the CGA oligonucleotides bound to the surface of the cell to form the nascent tetranucleotide ACGA.

Figure 24:
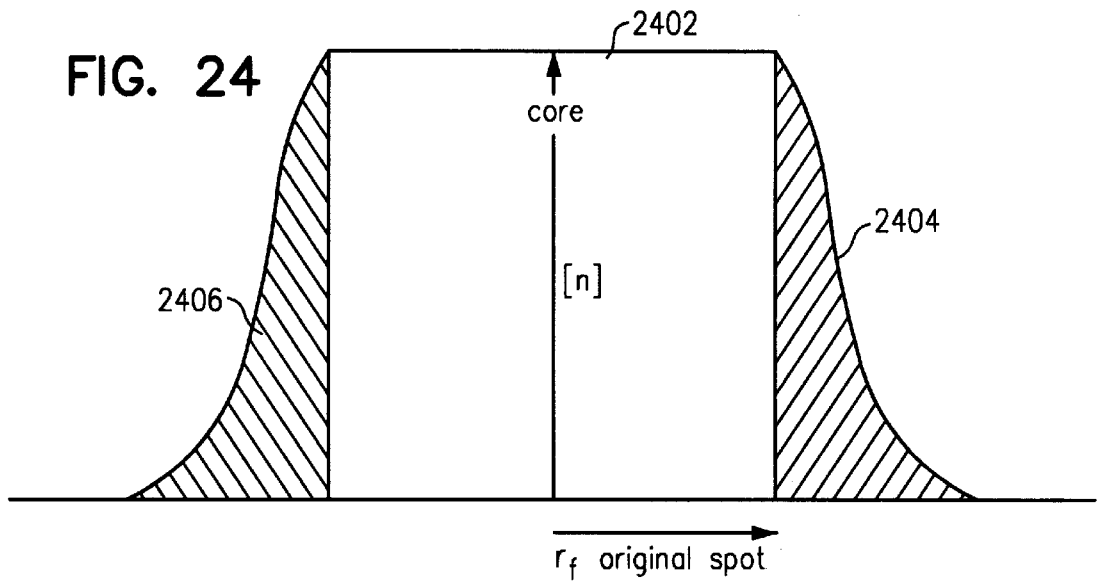

FIG. 24 shows a graphical representation of the contents of the surface of the HDA in the vicinity of the cell, similar to the representation in FIG. 17. Because of the improved technique, the core region 2402 containing predominately the oligonucleotide ACGA encompasses the entire surface of the cell. However, as in FIG. 17, the cell is surrounded by a penumbral region 2404 and 2406, containing a complex mixture of subsequences and deletion sequences of the oligonucleotide sequence ACGA. Thus, employing larger volume protected nucleoside phosphoramidite solution droplets following application of the initial droplet that defines the size, shape, and location of the cell eliminates the peripheral regions of the cell (1704 and 1706 in FIG. 17) that may contain deletion subsequences of the oligonucleotide intended to be synthesized on a cell. The improved technique does not, however, eliminate the penumbral regions.

In the example illustrated in FIGS. 18–24, the second and all subsequent droplets were applied with greater volumes than the volume of the first droplet. In general, larger volumes are effectively covering volumes. A covering volume is a volume sufficient to cover the area of a molecular array element even when a droplet having a covering volume is misregistered with respect to the molecular array element. It may also be the case that similarly sized, or even smaller volumes can be covering volumes. For example, if the surface characteristics of the molecular array substrate are changed following application of the first droplet that essentially defines the molecular array element, then subsequently applied droplets having the same volume as the first droplet may not adsorb as effectively to the molecular array substrate and may therefore end up distributed over a larger surface area than the surface area covered by the first droplet. In such cases, the second and subsequent droplets may have covering volumes even though their volumes are identical to that of the first droplet. Even smaller volumes may be covering volumes. The first-described improved technique relates to applying the second and subsequent droplets with covering volumes sufficient to ensure that, after the second and subsequent droplets spread out radially from their point of application, they will completely cover the area of the molecular array element, despite misregistration.

Figure 25:
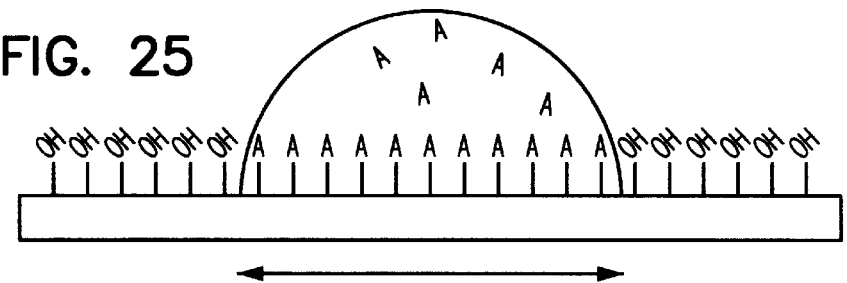
FIGS. 25–31 illustrate a second improved technique for application of protected nucleoside phosphoramidite solution droplets to the surface of the HDA.
Figure 26:
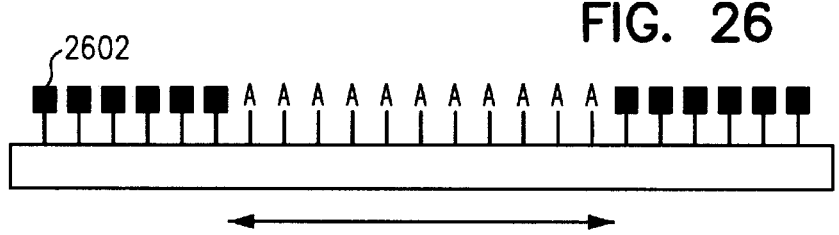
Figure 27:
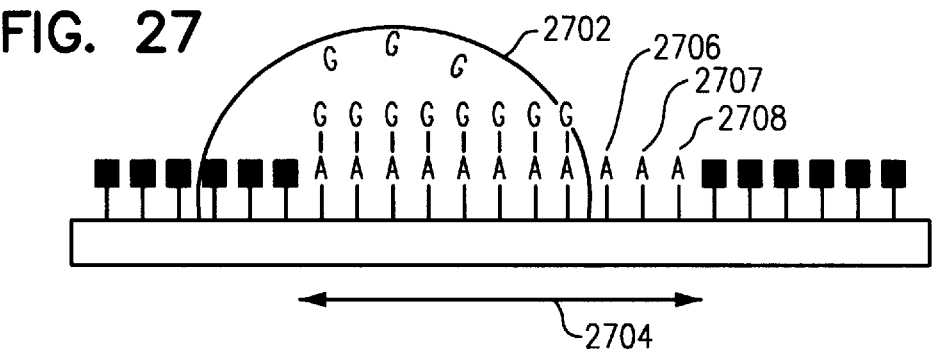

FIGS. 25–31 illustrate a second improved technique for application of protected nucleoside phosphoramidite solution droplets to the surface of the HDA. FIG. 25 illustrates application of an initial protected adenosine phosphoramidite solution droplet to the surface of the HDA. FIG. 25 is identical to FIG. 18. FIG. 26 represents the surface of the HDA in the vicinity of the droplet applied in FIG. 25 following a capping step analogous to the acetylating step employed in FIGS. 19 and 10A. However, this initial capping step employs a much more efficient capping agent, represented in FIG. 26 and subsequent figures sa filled in square, such as cap 2602. The capping agent binds to free OH groups on linker molecules to prevent them from subsequently binding to protected nucleoside phosphoramidites in subsequent steps. In FIG. 27, a second droplet containing protected guanosine phosphoramidite is applied to the cell. As in FIGS. 20 and 11A, the second droplet 2702 is offset to the left of the cell, described by the double arrow 2704. Note that the second droplet 2702 is of the same volume as the initial droplet applied in FIG. 25. Thus, deprotected substrate-bound adenosine 2706–2708 within the cell is not exposed to the second droplet 2702. However, unlike in FIGS. 20 and 11A, there are no free linker OH groups available for binding the protected guanosine phosphoramidite.

Figure 28:
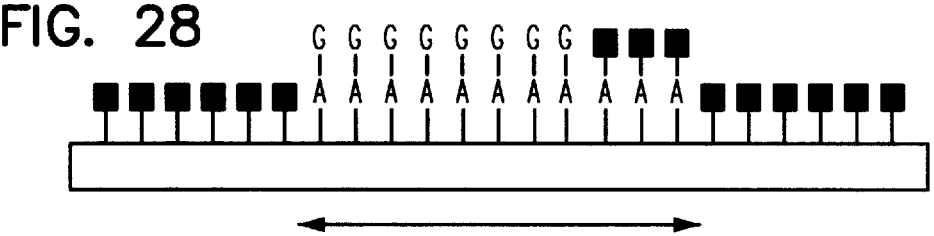
Figure 29:
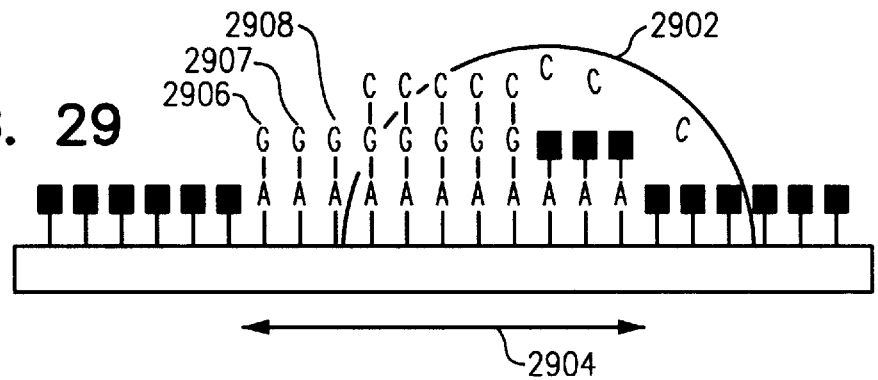
Figure 30:
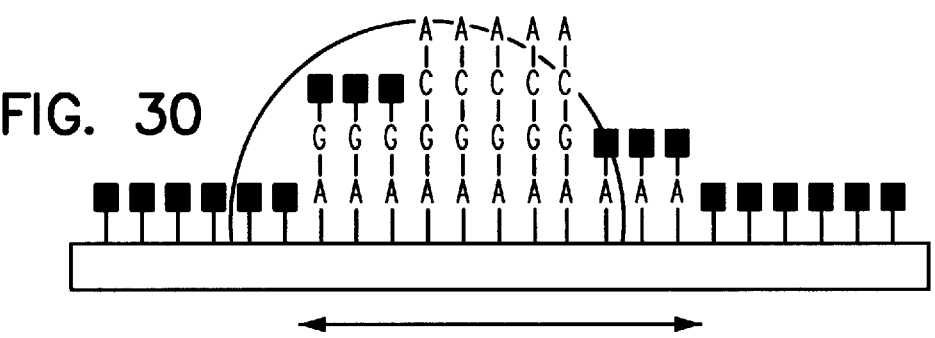
Figure 31:
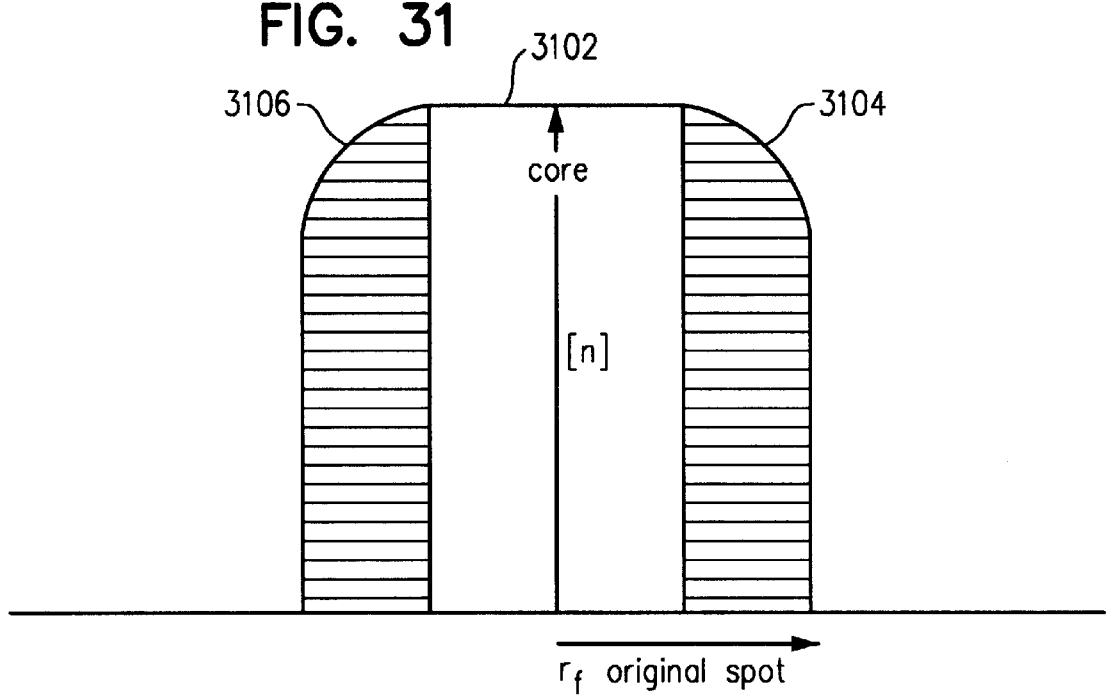

FIG. 28 illustrates the surface of the HDA in the vicinity of the cell following a second capping step. FIG. 29 shows application of a third droplet containing protected cytosine phosphoramidite following a deprotection step, as in FIGS. 22 and 13A. As in FIGS. 22 and 13A, the third droplet 2902 is offset to the right of the cell indicated in FIG. 29 by double arrow 2904. Thus, certain deprotected 5'-guanosine subunits 2906–2908 are not in contact with the solution of the third droplet 2902 and thus are not extended in a third nucleoside addition step. Finally, FIG. 30 shows the location of a fourth, misregistered, protected adenosine phosphoramidite solution droplet to the surface of the HDA. FIG. 31 represents the resulting surface-bound oligonucleotide content of the cell of the HDA, similar to the representations of FIG. 17 and 24. As a result of using a more effective capping agent in the first capping step, or in the first few capping steps of the second technique, the cell is not surrounded by a penumbral region, as were the cells resulting from the earlier techniques, 1708 and 1710 in FIG. 17 (2404 and 2406 in FIG. 24). However, as in FIG. 17, the cell contains a core region 3102 surrounded by a peripheral region 3104 and 3106. The core region contains primarily the tetranucleotide ACGA along with much smaller amounts of the oligonucleotides CGA and GA and the nucleotide A. By using a more effective capping agent, many of the partial sequence oligonucleotides contained in the core 1702 of FIG. 17, as discussed above, have been eliminated from the core 3102 of FIG. 31. However, a peripheral region 3104 and 3106 may still contain deletion subsequences that lead to a decreased signal-to-noise ratio and potentially false results. Thus, by employing the second improved technique of using a more effective capping agent in the first capping step or first few capping steps, the penumbral regions surrounding a cell can be eliminated.

Figure 32:
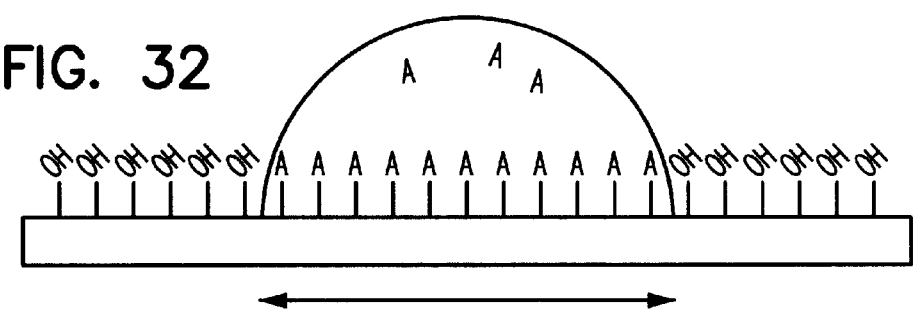
FIGS. 32–38 illustrate a third improved technique for applying protected deoxynucleoside phosphoramidite solution droplets to an HDA.
Figure 33:
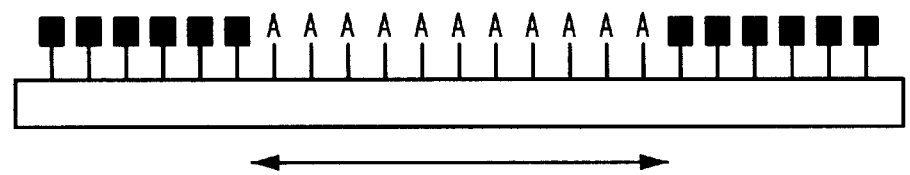
Figure 34:
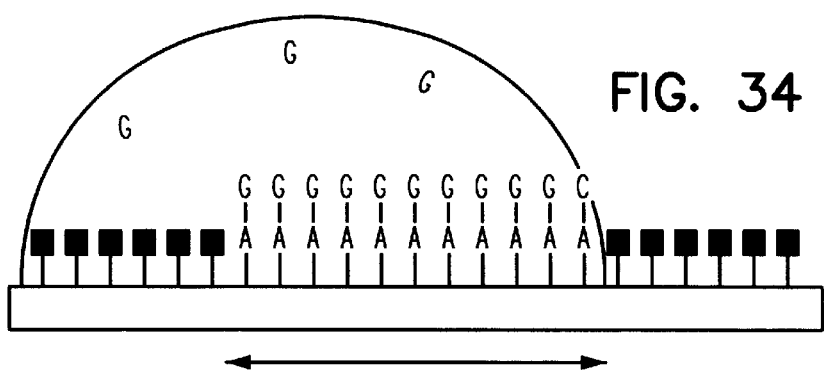
Figure 35:
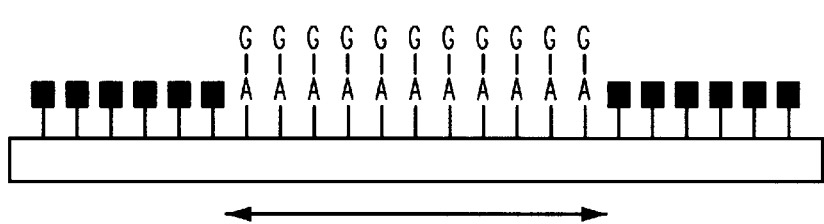
Figure 36:
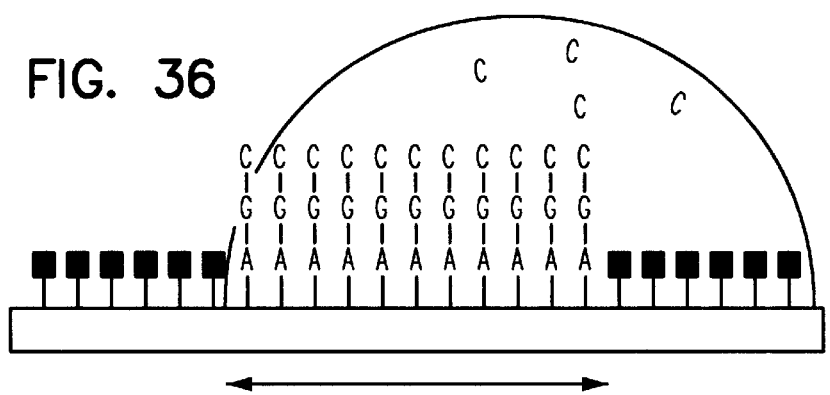
Figure 37:
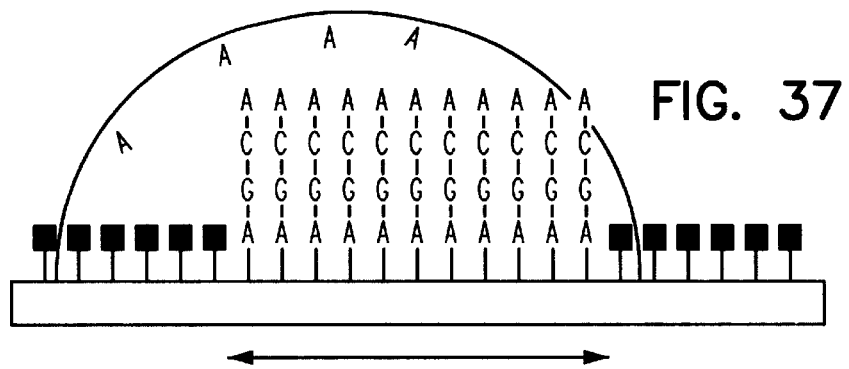
Figure 38:
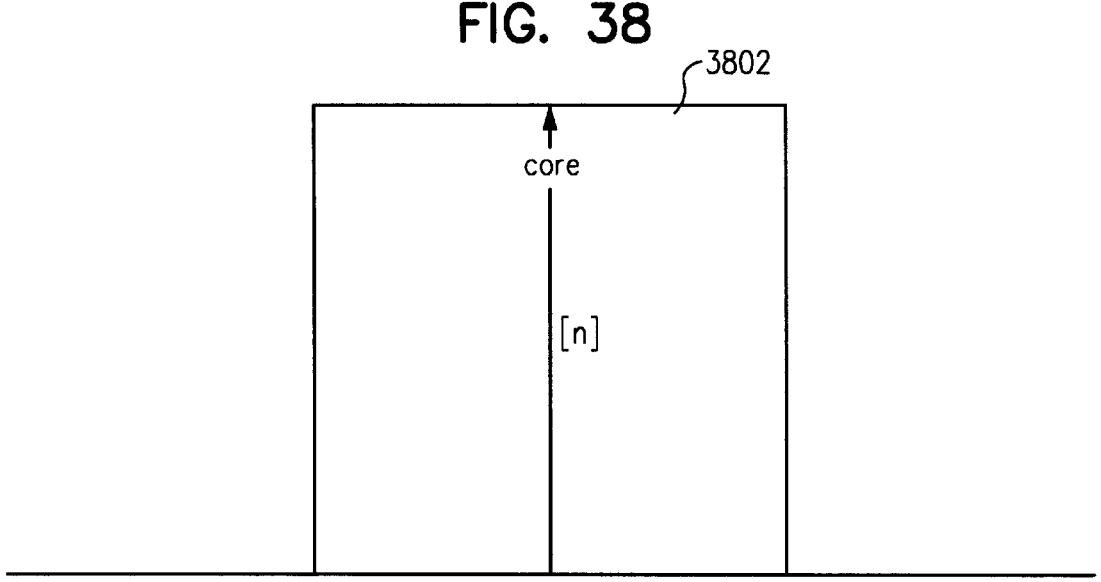

FIGS. 32–38 illustrate a third improved technique for applying protected deoxynucleoside phosphoramidite solution droplets to an HDA that is a combination of the first improved technique, described in FIGS. 18–24, and the second improved technique described in FIGS. 25–31. This third improved technique is the preferred embodiment of the present invention. In FIG. 32, an initial protected deoxyadenosine phosphoramidite solution is applied to the surface of the HDA to define a cell, as in FIGS. 9A, 18, and 25. In FIG. 33, the more efficient capping step is carried out to deactivate any free linker OH groups. In FIG. 34, a droplet having a covering volume that contains protected deoxyguanosine phosphoramidite is applied, off-center, to the cell defined by application of the initial droplet in FIG. 32. This results in addition of a guanosine subunit to all of the substrate-bound adenosine within the cell. FIG. 35 shows the cell following a second capping step. FIG. 36 shows the application of a third protected deoxycytosine phosphoramidite solution droplet to the HDA. Again, because the third droplet has a covering volume, even though the third droplet has been applied off-center, the entire surface of the cell is exposed to the protected deoxycytosine phosphoramidite. This results in efficient addition of cytosine to the deprotected 5'-guanosine on the surface of the cell. Finally, FIG. 37 shows application of a fourth droplet containing protected deoxyadenosine phosphoramidite to the cell. Again, the fourth droplet has a covering volume with respect to the area of the molecular array element defined by application of the initial droplet applied in FIG. 32. Thus, all of the deprotected cytosine subunits on the surface of the cell are exposed to the protected deoxyadenosine phosphoramidite, resulting in efficient synthesis of the oligonucleotide ACGA. FIG. 38 graphically represents the contents of the cell following the steps illustrated in FIGS. 32–37. The use of droplets having covering volumes following the application of the initial droplet has, as in the first improved method described in FIGS. 18–24, eliminated the peripheral region of the cell (1704 and 1706 in FIG. 17 and 3104 and 3106 in FIG. 31). The use of the improved capping agent during the first capping step, or during the first few capping steps, as in the second improved technique described in FIGS. 25–31, has eliminated the penumbral regions surrounding the cell (1708 and 1710 in FIG. 17, 2404 and 2406 in FIG. 24). Thus, the cell contains a central core region 3802 that primarily contains the oligonucleotide ACGA along with smaller amounts of A, GA, and CGA, and there are no penumbral regions adjacent to the cell. Thus, the preferred technique eliminates the decrease in signal-to-noise ratio and false results arising from contaminating oligonucleotides in peripheral and penumbral regions that result from employing the currently available technique described in FIGS. 917.

Figure 5A:
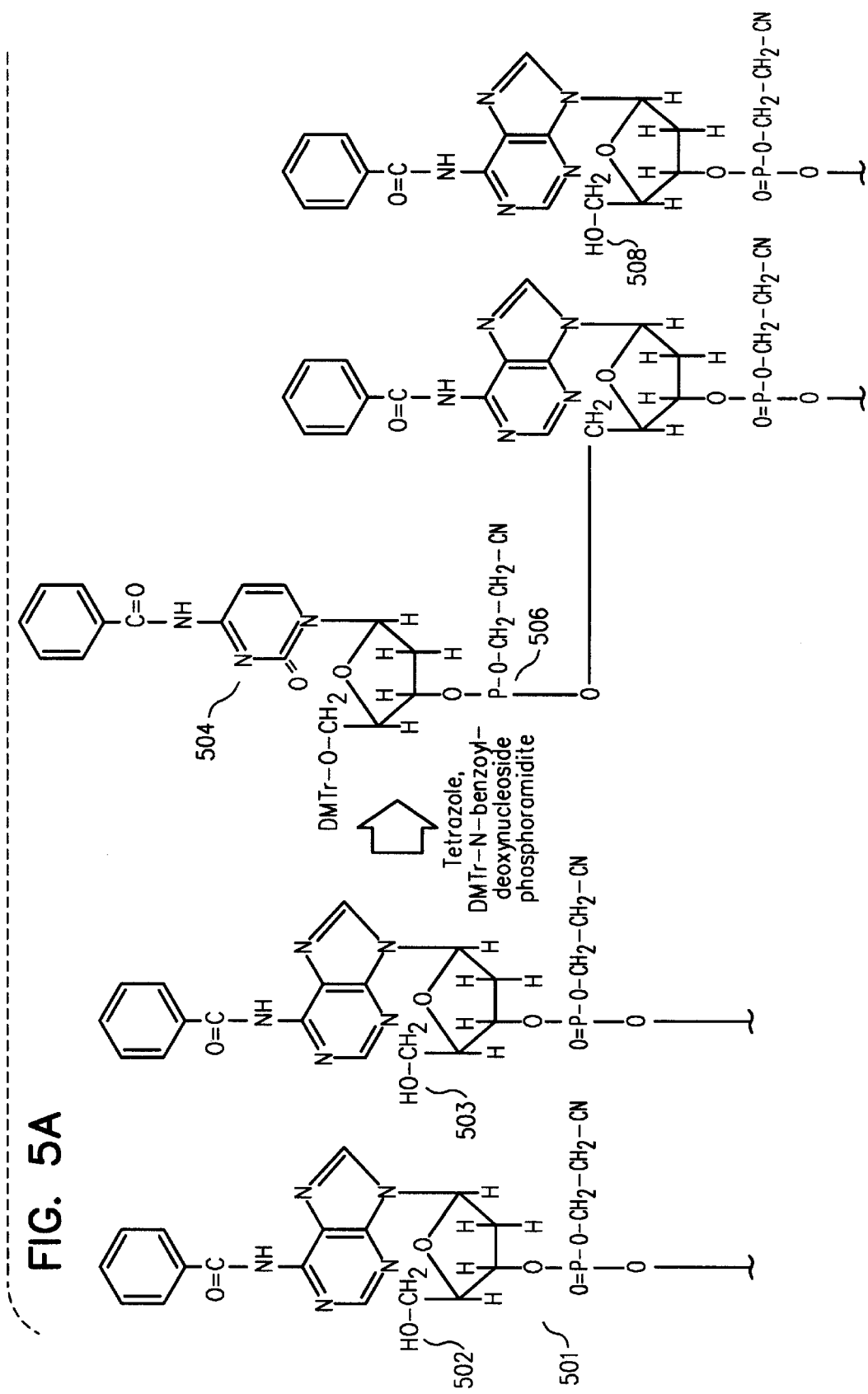
FIGS. 5A and 5B illustrates the addition of a deoxynucleoside phosphoramidite monomer to a growing oligonucleotide polymer bound to the surface of a high-density array.
Figure 5B:
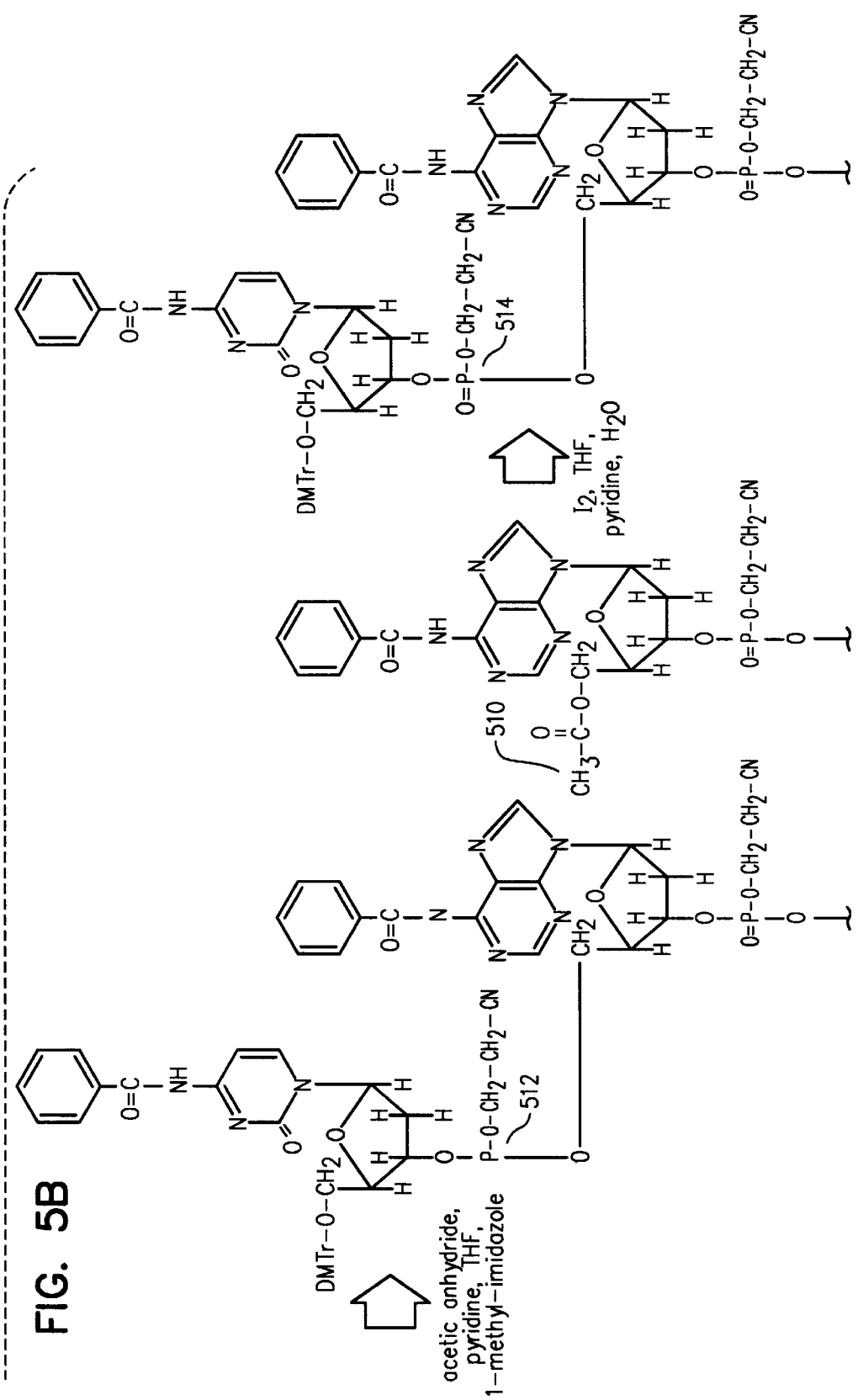

In one embodiment of the present invention, 1 ml (1g, 4.5 mmoles) of diethoxy-N,N-diisopropyl phosphoramidite ("DEDIP") (Chemgene RN-1410) is dissolved in 45 ml of anhydrous acetonitrile (Aldrich 27,100-4) to produce a DEDIP solution. The embodiment uses a commercial solution of activator ("ACT") (0.45 M tetrazole in acetonitrile, Glen Research 30–3100, or 0.25M 5-ethylthio-1H-tetrazole in acetonitrile, Glen Research 30-3140 or 0.25M 4,5-dicyanoimidazole in acetonitrile, Glen Research 30–3150, or any other activator used for the coupling step in DNA synthesis). Both DEDIP and ACT solutions are loaded, mixed or separately, in a DNA array synthesizer. Each sequence of nucleotide addition steps, such as the steps illustrated in FIGS. 5A–B, is started by deblocking the dimethoxytrityl that is present on the 5' end of the nascent substrate-bound oligonucleotide. This is done by flooding the HDA with a deblocking or deprotecting solution ("DPROT solution") commonly used on DNA synthesizers (3% trichloroacetic acid in dichloromethane, Glen Research 40-4140). Then one or a few droplets of the phosphoramidite to be added, premixed or not, are fired from a valve, thermal Ink-Jet, or piezo head onto the HDA. After a few minutes, the surface of the HDA is washed. The capping solution used in the first capping step, or first few capping steps, of this embodiment, a mixture of the DEDIP and ACT solutions, is different than the conventional CAP A/CAP B solutions employed in current techniques and employed in later capping steps in the present embodiment. A discussed above, the DEDIP and ACT capping solution used in the capping steps of this embodiment, although more expensive than CAP A/CAP B solutions, is much more efficient at capping free linker hydroxyls (greater than 90% efficiency) and unreacted deprotected 5' hydroxyls of nascent oligonucleotides (greater than 98% efficiency). The remaining steps (oxidizing, deblocking, and washing) are performed according to conventional oligonucleotide synthesis, with the exception that, as discussed above, larger sized droplets of phosphoramidite solutions are applied subsequent to application of the first, cell-defining droplet.

An alternative potential capping phosphoramidite could be used as follows: 1 ml (1g, 4.1 mmoles) of diallyl-N,N-diisopropyl phosphoramidite (DADIP) (Aldrich 43,960-6) dissolved in 41 ml of anhydrous acetonitrile (Aldrich 27,100-4). Other alternative capping solutions are possible. For example, any of a number of small phosphoramidites having the formula $(R^1-O-)(R^2-O-)P-(NH(CH(CH_3)_2)_2$ can be used in the capping solution, where $R^1$ and $R^2$ are the same, or different, side chains that may include various functional groups such as carboxyls or one or more unsaturated bonds. For a negatively charged surface, the phosphoramidite dicyanoethyl-N,N-diisopropyl phosphoramidite can be used. Long-chain alkyl $R^1$ and $R^2$ side chains can be used for a hydrophobic surface.

Although the present invention has been described in terms of a particular embodiment, it is not intended that the invention be limited to this embodiment. Modifications within the spirit of the invention will be apparent to those skilled in the art. For example, the preferred embodiment of the current invention relates to synthesis of substrate-bound oligonucleotides, but the techniques of the current invention may be applied in synthesizing other types of polymers. Application of droplets having covering volumes can be employed in the step-wise synthesis of any substrate bound polymers within cells or elements of molecular arrays. As discussed in previous sections, covering volumes may be greater, similar to, or smaller than the volume of the first applied droplet. In some cases, the covering volume may change with application of each successive droplet. In the synthesis of polymers other than oligonucleotides, employment of very efficient chain termination and surface deactivation agents during surface deactivation following binding of a first monomer to a solid substrate, such as the DEDIP and ACT solutions used in the described embodiment, can lead to more distinctly formed cells having a more consistent concentration of a desired surface-bound polymer. In a preferred embodiment, the more expensive, highly efficient capping agent is employed only in the first surface deactivation step, or in the first few surface deactivation and unreacted polymer termination steps. However, where the cost of reagents is not a limiting concern, the expensive, highly efficient capping agent may be employed for any number of capping steps.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

What is claimed is:

1. An improved method for repeatedly applying solutions of reactive nucleotide monomers to a particular feature on a chemically-prepared surface of a solid substrate of a molecular array in order to synthesize a substrate-bound oligonucleotide polymer within the feature having a predetermined monomer sequence, the method comprising:

applying an initial volume of an initial solution of a reactive nucleotide monomer to the feature to react with reactive substrate-bound groups of the feature to produce a nascent substrate-bound oligonucleotide polymer within a region of the surface of the solid substrate in contact with the initial volume of solution;

capping unreacted reactive substrate-bound groups of the chemically-prepared surface of the solid substrate by applying a solution of a reactive capping agent to the surface of the solid substrate; and repeatedly applying a solution containing an activating agent to the feature in order to activate nascent oligonucleotide polymers within the feature for reaction with a subsequently applied reactive nucleotide monomer;

applying an additional coverings volume of a solution of a reactive nucleotide monomer to the feature in order to chemically bind the reactive nucleotide monomer to the nascent polymers within the feature; and capping unreacted activated nascent oligonucleotide polymers and any remaining unreacted reactive substrate-bound groups of the chemically-prepared surface of the solid substrate by applying a solution of a reactive capping agent to the feature.

2. The method of claim 1 wherein the capping agent initially used to cap unreacted reactive substrate-bound groups of the chemically-prepared surface of the solid substrate reacts with greater than 90% efficiency with unreacted reactive substrate-bound groups of the chemically-prepared surface of the solid substrate and reacts with greater than 95% efficiency with unreacted activated nascent oligonucleotide polymers.

3. The method of claim 2 further including:

rinsing the surface of the feature following application of a solution of reactive nucleotide monomer;

rinsing the surface of the feature following each application of a solution to a reactive capping agent to the surface of the substrate;

rinsing the surface of the feature following each application of a solution containing an activating agent to the surface of the solid substrate.

4. The method of claim 2 wherein the reactive monomers are 5'-protected deoxynucleoside phosphoramidites.

5. The method of claim 4 wherein a deoxynucleoside phosphoramidite is 5' protected by covalent bonding of a dimethoxytrityl group to the 5'-hyrdoxyl oxygen of the deoxynucleoside phosphoramidite.

6. The method of claim 4 wherein the capping agent initially used to cap unreacted reactive substrate-bound groups of the chemically-prepared surface of the solid substrate solution comprises a mixture of a first solution of approximately 0.1 M phosphoramidite in anhydrous acetonitrile and a second solution comprising an activator in acetonitrile.

7. The method of claim 6 wherein the phosphoramidite is selected from among the group of phosphoramidites consisting of:

diethoxy-N,N-diisopropyl phosphoramidite;

diallyl-N,N-diisopropyl phosphoramidite;

a phosphoramidite having the formula $(R^1—O—)(R^2—O)P—N(CH(CH_3)_2)_2$ where $R^1$ and $R^2$ may be similar or different alkyl side chains, side chains having a carboxylic group, and side chains with a double bond; and dicyanoethyl-N,N-diisopropyl phosphoaramidite.

8. The method of claim 6 wherein the activator is selected from among the group of activators consisting of:

0.45 M tetrazole;

0.25 M 5-ethylthio-1H-tetrazole; and 0.25 M 4,5-dicyanoimidazole.

9. The method of claim 4 wherein the solution containing an activating agent comprises 3% acid in a solvent, wherein the acid is selected from among trichloroacetic acid and dichloroacetic acid, and wherein the solvent is selected from among dichloromethane and toluene.

10. The method of claim 4 further including:

following the reaction of each applied 5'-protected deoxynucleoside phosphoramidite reactive monomer, the 3'-phosphite group of the applied 5'-protected deoxynucleoside phosphoramidite linking the applied 5'-protected deoxynucleoside to a target hydroxyl oxygen atom is oxidized by application of an oxidizing solution to a phosphate group; and the oxidizing solution is rinsed from the surface of the substrate following oxidation of the phosphite group.

11. The method of claim 1 used in an apparatus for automated production of molecular arrays.

12. A molecular array comprising a number of features on the surface of a substrate containing substrate-bound polymers produced by the method of claim 1.

13. An improved method for repeatedly applying solutions of reactive nucleotide monomers to a particular feature on a solid substrate of a molecular array in order to synthesize a substrate-bound oligonucleotide polymer within the feature having a predetermined monomer sequence, the method comprising:

applying an initial volume of an initial solution of a reactive nucleotide monomer to the feature to react with reactive substrate-bound groups of the chemically-prepared surface within the feature in a region of the surface of the solid substrate in contact with the initial volume of solution;

capping unreacted reactive substrate-bound groups of the chemically-prepared surface of the solid substrate within the feature by applying a solution of a reactive capping agent to the feature that reacts with greater than 90% efficiency with unreacted reactive substrate-bound groups of the chemically-prepared surface of the solid substrate; and repeatedly applying a solution containing an activating agent to the feature in order to activate nascent oligonucleotide polymers for reaction with a subsequently applied reactive nucleotide monomer;

applying an additional volume of a solution volume of a solution of a reactive nucleotide monomer to the feature in order to chemically bind the reactive monomer to the nascent polymers within the feature; and capping unreacted activated nascent oligonucleotide polymers and any remaining unreacted reactive substrate-bound groups of the chemically-prepared surface feature by applying a solution of a reactive capping agent to the feature.

14. The method of claim 13 wherein the additional covering volume of a solution of a reactive nucleotide monomer applied to the feature ensures that the additional volume of the solution will spread out the completely cover the surface containing nascent oligonucleotide polymers produced by application of the initial volume of the initial solution.

15. The method of claim 14 wherein the reactive monomers are 5'-protected deoxynucleoside phosphoramidites.

16. The method of claim 15 wherein the capping agent initially used to cap unreacted reactive substrate-bound groups of the chemically-prepared surface of the solid substrate solution comprises a mixture of a first solution of approximately 0.1 M phosphoramidite in anhydrous acetonitrile and a second solution comprising an activator in acetonitrile.

17. The method of claim 16 wherein the phosphoramidite is selected from among the group of phosphoramidites consisting of:

diethoxy-N,N-diisopropyl phosphoramidite;

diallyl-N,N-diisopropyl phosphoramidite;

a phosphoramidite having the formula $(R^1-O-)(R^2-O-)P-N(CH(CH_3)_2)_2$ where $R^1$ and $R^2$ may be similar or different alkyl side chains, side chains having a carboxylic group, and side chains with a double bond; and dicyanoethyl-N,N-diisopropyl phosphoaramidite;

and wherein the activator is selected from among the group of activators consisting of:

0.45 M tetrazole;

0.25 M 5-ethylthio-1H-tetrazole; and 0.25 M 4,5-dicyanoimidazole.

18. A molecular array comprising a number of features on the surface of a substrate containing substiate-bound polymers produced by the method of claim 13.

19. The method of claim 13 used in an apparatus for automated production of molecular arrays.

* * * * *